United States Patent [19]

Bundy

[11] 4,218,378

[45] Aug. 19, 1980

[54] 11A-METHANO-TXA COMPOUNDS

[75] Inventor: Gordon L. Bundy, Portage, Mich.

[73] Assignee: The Upjohn Company, Kalamazoo, Mich.

[21] Appl. No.: 35,143

[22] Filed: May 1, 1979

[51] Int. Cl.² ............... C07D 301/00; C07D 303/00; C09F 5/08; C11C 1/00
[52] U.S. Cl. ................................. 260/333; 260/410; 260/410.5; 260/410.9 R; 260/413; 260/408; 556/416; 260/326.5 D; 260/239 B; 260/239 BF; 542/416; 542/421; 544/147; 544/376; 546/269; 546/207; 560/51; 560/53; 560/126; 562/452; 562/459; 562/463; 562/472; 562/507; 562/508; 568/329; 568/377
[58] Field of Search ............... 260/33; 542/413, 426, 542/427

[56] References Cited

U.S. PATENT DOCUMENTS 4,107,427  8/1978  Kelly .................................. 560/177

OTHER PUBLICATIONS

Samuelson, B. et al., edt., Advances in *Prostaglandin and Thromboxane Research* (New York), p. 5.

*Primary Examiner*—John F. Niebling
*Attorney, Agent, or Firm*—Robert A. Armitage

[57] ABSTRACT

The present invention provides novel 11a-methano-TXA compounds and intermediates and processs for their preparation. Further provided are methods for using these novel TXA analogs as inhibitors of thromboxane synthetase, rendering these analogs useful for a variety of pharmacological purposes. These pharmacological uses include anti-inflammatory, anti-thromobitc, and anti-asthma indications.

89 Claims, No Drawings

11A-METHANO-TXA COMPOUNDS

DESCRIPTION

1. Technical Field

The present invention relates to novel compositions of matter. Further, the present invention provides novel processes for preparing these compositions of matter. Moreover there are provided novel methods by which such compositions of matter are employed for pharmacologically useful purposes.

The present invention is specifically concerned with novel analogs of thromboxane $A_2$.

Structurally, thromboxane $A_2$ or $TXA_2$ has the structure and carbon atom numbering indicated by Formula I. $TXA_2$ undergoes spontaneous hydrolysis to thromboxane $B_2$, a compound whose structure and carbon-atom numbering are provided in formula II. As is apparent by reference to Formula II, $TXB_2$ may alternatively be named as 11a-homo-11a-oxa-PGF$_{2\alpha}$. For comparative purposes, the structure of PGF$_{2\alpha}$ or prostaglandin F$_{2\alpha}$ is provided in Formula III. For a discussion of the biological preparation of $TXA_2$ and $TXB_2$, see Samuelsson, Proceedings of the National Academy of Sciences USA 71:3400-3404 (1974) and M. Hamberg, et al., Proceedings of the National Academy of Sciences USA 72:2994 (1975). For a discussion of the chemical production of thromboxane $B_2$ and numerous analogs thereof, see U.S. Pat. No. 4,070,384, issued Jan. 24, 1978.

For a detailed discussion of related prostaglandins, such as prostaglandin F$_{2\alpha}$ of formula III, see Bergstrom, et al., Pharmacological Reviews 20:1 (1968).

As is apparent by reference to Formulas I, II, and III, $TXA_2$, $TXB_2$, and PGF$_{2\alpha}$ exhibit several asymmetric carbon atoms and these molecules may therefore exist in either racemic (optically inactive) form or in either of two optically active enantiomeric forms, i.e., the dextrorotatory and levorotatory forms. As represented in Formulas I, II, and III, the particular optically active form of $TXA_2$, $TXB_2$, and PGF$_{2'}$ obtained from biological sources is the isomer represented by these formulas. For convenience hereinafter, use of the term thromboxane or "TX" will refer to the optically active form of the thromboxane-type compound thereby referred to with the same absolute configuration as $TXA_2$, $TXB_2$, or PGF$_{2\alpha}$ obtained from biological sources.

The term "thromboxane intermediate" used herein refers to any heterocyclic or acyclic compound which is useful in preparing the various analogs of thromboxane $A_2$ disclosed herein. When a formula is used to depict a thromboxane intermediate, each such formula represents the particular stereoisomer of the thromboxane intermediate which is useful in preparing the TX analog of the same relative stereochemical configuration as $TXA_2$ obtained from biological sources.

The term "thromboxane-type" (TX-type) product, as used herein, refers to each of the various heterocyclic derivatives herein which are useful pharmacologically, as indicated hereinafter. The formulas, as drawn herein, which depict the thromboxane-type product, each represent the particular stereoisomer of that product which is of the same relative stereochemical configuration as $TXA_2$ obtained biosynthetically. The term "thromboxane analog", as used herein, refers to that stereoisomer of a TXA-type product which is of the same relative stereochemical configuration as $TXA_2$ obtained from biological sources or a mixture comprising that stereoisomer and the enantiomer thereof. In particular, where a formula is used to depict a thromboxane-type product herein, the term thromboxane analog refers to the compound of that formula or mixture comprising that compound and the enantiomer thereof.

2. Prior Art

As indicated above, thromboxane $A_2$ is known in the art. See Hamberg and Samuelsson, cited above. Likewise, numerous analogs of thromboxane $B_2$ and their use as reproductive cycle control agents is known in the art. See U.S. Pat. No. 4,070,384, issued Jan. 24, 1978.

Further, certain 11-oxa prostaglandin-type compounds are known in the art. See particularly Belgian Pat. No. 830,423 (Derwent Farmdoc CPI No. 01971X) and Tetrahedron Letters 43:3715-3718 (1975).

Other heterocyclic ring analogs of the prostaglandins include the $9\alpha,11\alpha$- or $11\alpha,9\alpha$-epoxymethano-9,11-dideoxy-PGF-type compounds described in U.S. Pat. Nos. 3,950,363 and 4,028,354. Finally related azo and epoxyimino compounds are known in the art. See U.S. Pat. No. 4,112,224.

Further known in the art are the cyclohexane analogs of PGF$_{2\alpha}$ and PGE$_2$, e.g., 10a-homo-PGF$_{2\alpha}$ and 10a-homo-PGE$_2$. See Crossley, N. S., Tett. Lett. 36:3327-3330 (1971). Also racemic 11a-homo-PGE$_1$ is described by Floyd, M. B., et al., J. Org. Chem. 44:71-75 (1979). A related cyclohexene is described by Muchowski, J. M., et al., Prostaglandins 75:297-302 (1975) and certain 11-deoxy-11a-homo PG's are described in Derwent Farmdoc CPI 29086Y, abstracting French Pat. No. 2,327,768.

SUMMARY OF THE INVENTION

The present invention particularly provides:

(1) a thromboxane analog of formula IV wherein $Y_1$ is (1) trans—CH═CH—,
(2) cis—CH═CH—,
(3) —CH$_2$CH$_2$—, or
(4) —C≡C—, wherein $M_1$ is $\alpha$-R$_5$:$\beta$-OH, $\alpha$-OH:$\beta$-R$_5$, or $\alpha$-H:$\beta$-H, wherein R$_5$ is hydrogen or methyl, and wherein L$_1$ is $\alpha$-R$_3$:$\beta$-R$_4$, $\alpha$-R$_4$:$\beta$-R$_3$, or a mixture of $\alpha$-R$_3$:$\beta$-R$_4$ and $\beta$-R$_3$:$\alpha$-R$_4$, wherein R$_3$ and R$_4$ are hydrogen, methyl, or fluoro, being the same or different, with the proviso that one of R$_3$ and R$_4$ is fluoro only when the other is hydrogen or fluoro, or wherein —C(M$_1$)—C(L$_1$)— is trans—CH═CH—; wherein Z$_1$ is (1) cis—CH═CH—CH$_2$—(CH$_2$)$_g$—CH$_2$—,
(2) cis—CH═CH—CH$_2$—(CH$_2$)$_g$—CF$_2$—,
(3) cis—CH$_2$—CH═CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —(CH$_2$)$_2$-O-(CH$_2$)$_g$—CH$_2$—, or
(8) trans—CH$_2$—(CH$_2$)$_g$—CH$_2$—CH═CH—;
(9) —(m-Ph)—O—(CH$_2$)$_g$—, or
(10) —(m-Ph)—CH$_2$—(CH$_2$)$_g$—, wherein g is one, 2, or 3 and —(m-Ph)— is meta-phenylene; wherein R$_7$ is (1) —(CH$_2$)$_m$—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;

(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different; wherein $X_1$ is (1) —COOR$_1$, wherein $R_1$ is
  (a) hydrogen;
  (b) alkyl of one to 12 carbon atoms, inclusive;
  (c) cycloalkyl of 3 to 10 carbon atoms, inclusive;
  (d) aralkyl of 7 to 12 carbon atoms, inclusive;
  (e) phenyl;
  (f) phenyl substituted with one, two, or three chloro or alkyl of one to 3 carbon atoms;
  (g) phenyl substituted in the para position by
    (i) —NH—CO—R$_{25}$
    (ii) —CO—R$_{26}$
    (iii) —O—CO—R$_{27}$
    (iv) —CH=N—NH—CO—NH$_2$
  wherein $R_{25}$ is methyl, phenyl, acetamidophenyl, benzamidophenyl, or —NH$_2$; $R_{26}$ is hydroxy, methyl, phenyl, —NH$_2$, or methoxy; and $R_{27}$ is phenyl or acetamidophenyl; inclusive, or a pharmacologically acceptable salt thereof when $R_1$ is hydrogen;
(2) —CH$_2$OH;
(3) —COL$_4$, wherein L$_4$ is
  (a) amino of the formula —NR$_{21}$R$_{22}$, wherein R$_{21}$ and R$_{22}$ are
    (i) hydrogen;
    (ii) alkyl or one to 12 carbon atoms, inclusive;
    (iii) cycloalkyl of 3 to 10 carbon atoms, inclusive;
    (iv) aralkyl of 7 to 12 carbon atoms, inclusive;
    (v) phenyl;
    (vi) phenyl substituted with one, 2, or 3 chloro, alkyl of one to three carbon atoms, inclusive, hydroxy, carboxy, alkoxycarbonyl of one to 4 carbon atoms, inclusive, or nitro;
    (vii) carboxyalkyl of 2 to 5 carbon atoms, inclusive;
    (viii) carbamoylalkyl of 2 to 5 carbon atoms, inclusive;
    (ix) cyanoalkyl of 2 to 5 carbon atoms, inclusive;
    (x) acetylalkyl of 3 to 6 carbon atoms, inclusive;
    (xi) benzoylalkyl of 7 to 11 carbon atoms, inclusive;
    (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    (xiii) pyridyl;
    (xiv) pyridyl substituted by one, 2, or 3 chloro, alkyl of one to 3 carbon atoms, inclusive, or alkoxy of one to 3 carbon atoms, inclusive;
    (xv) pyridylalkyl of 6 to 9 carbon atoms, inclusive
    (xvi) pyridylalkyl substituted by one, 2, or 3 chloro, alkyl of one to 3 carbon atoms, inclusive, hydroxy or alkoxy of one to 3 carbon atoms, inclusive;
    (xvii) hydroxyalkyl of one to 4 carbon atoms, inclusive;
    (xviii) dihydroxyalkyl of one to 4 carbon atoms, or
    (xix) trihydroxyalkyl of one to 4 carbon atoms;
    with the further proviso that not more than one of $R_{21}$ and $R_{22}$ is other than hydrogen or alkyl;
  (b) cycloamino selected from the group consisting of
    (i) pyrrolidino,
    (ii) piperidino,
    (iii) morpholino,
    (iv) piperazino,
    (v) hexamethyleneimino,
    (vi) pyrrolino,
    (vii) 3,4-didehydropiperidinyl, or
    (viii) pyrrolidino, piperidino, morpholino, piperazino, hexamethyleneimino, pyrrolino, or 3,4-didehydropiperidinyl substituted by one or two alkyl of one to 12 carbon atoms, inclusive;
  (c) carbonylamino of the formula —NR$_{23}$COR$_{21}$, wherein R$_{23}$ is hydrogen or alkyl of one to 4 carbon atoms and R$_{21}$ is other than hydrogen, but otherwise as defined above; or
  (d) sulfonylamino of the formula —NR$_{23}$SO$_2$R$_{21}$, wherein R$_{21}$ and R$_{23}$ are as defined in (c);
(4) —CH$_2$NL$_2$L$_3$, wherein L$_2$ and L$_3$ are hydrogen or alkyl of one to 4 carbon atoms, inclusive, being the same or different, or a pharmacologically acceptable acid addition salt thereof wherein $X_1$ is —CH$_2$NL$_2$L$_3$;

(2) a thromboxane intermediate of formula V, VI, VII, VIII, IX, or X, wherein L$_1$, M$_1$, R$_7$, Y$_1$, and Z$_1$ are as defined above; wherein M$_7$ is α-R$_5$:β-OR$_{10}$, α-OR$_{10}$:β-R$_5$, or α-H:β-H, wherein R$_{10}$ is a stable, acid hydrolyzable blocking group; and wherein R$_{12}$ is alkyl of one to 12 carbon atoms, inclusive, aralkyl of 7 to 12 carbon atoms, inclusive, aralkyl of 7 to 12 carbon atoms, inclusive; phenyl; or phenyl substituted with one, two, or three chloro or alkyl of one to 3 carbon atoms.

With regard to the divalent substituents described above (e.g., L$_1$ and M$_1$), these divalent radicals are defined as α-R$_i$:β-R$_j$, wherein R$_i$ represents the substituent of the divalent moiety in the alpha configuration with respect to the ring and R$_j$ represents the substituent of the divalent moiety in the beta configuration with respect to the plane of the ring. Accordingly, when M$_1$ is defined as α-OH:β-R$_5$, the hydroxy of the M$_1$ moiety is in the alpha configuration, i.e., as in TXA$_2$ above, and the R$_5$ substituent is in the beta configuration. Not all carbon atoms to which such divalent moieties are attached represent asymmetric centers. For example when both valence bonds are to hydrogen (e.g., L$_1$ or M$_1$ is α-H:β-H), then no asymmetric center is present.

All the novel thromboxane analogs herein are named as 11a-methano-TXA compounds by virtue of the substitution of methylene for oxa at C-11a (refer to formula I). Moreover, when M$_1$ is α-H:β-H, the thromboxane analogs are further described as 11a-methano-15-deoxy-TXA compounds, since the C-15 hydroxy of thromboxane A$_2$ is also absent from such compounds. Finally when —C(M$_1$)—C(L$_1$)— is trans—CH=CH—, the novel thromboxane analogs are all characterized as 11a-methano-15,16-didehydro-15-deoxy-TXA compounds.

When R$_5$ is methyl, the thromboxane analogs are all named as "15-methyl-TXA" compounds. Further, except for compounds wherein Y$_1$ is cis—CH=CH—, compounds wherein the M$_1$ moiety contains an hydroxyl in the beta configuration are additionally named as 15-epi-TXA compounds. For the compounds wherein $Y_1$ is cis—CH═CH—, then only compounds wherein the $M_1$ moiety contains an hydroxyl in the alpha configuration are named as 15-epi-TXA compounds. For a description of this convention of nomenclature for identifying C-15 epimers, see U.S. Pat. No. 4,016,184, issued Apr. 5, 1977, particularly columns 24-27 thereof.

Those TXA analogs herein wherein $Z_1$ is cis—CH═CH—CH$_2$—(CH$_2$)$_g$—CH$_2$— or cis—CH═CH—CH$_2$—(CH$_2$)$_g$—CF$_2$— are named as "TXA$_2$" compounds. The latter compounds are further characterized as "2,2-difluoro-TXA$_2$-type" compounds. When g is 2 or 3, the prostaglandin analogs so described are "2a-homo" or "2a,2b-dihomo" compounds, since in this event the $X_1$ terminated side chain contains 8 or 9 carbon atoms, respectively, in place of the 7 carbon atoms contained in PGF$_{2\alpha}$. These additional carbon atoms are considered as though they were inserted between the C-2 and C-3 positions. Accordingly, these additional carbon atoms are referred to as C-2a and C-2b, counting from the C-2 to the C-3 position.

Further, when $Z_1$ is —(CH$_2$)$_3$—(CH$_2$)$_g$—CH$_2$— or —(CH$_2$)$_3$—(CH$_2$)$_g$—CF$_2$—, wherein g is as defined above, the compounds so described are "TXA$_1$" compounds. When g is 2 or 3, the "2a-homo" and "2a,2b-dihomo" compounds are described as is discussed in the preceding paragraph.

When $Z_1$ is —CH$_2$—O—CH$_2$—(CH$_2$)$_g$—CH$_2$—, the compounds so described are named as "5-oxa-TXA$_1$" compounds. When g is 2 or 3, these compounds additionally so described as "2a-homo" or "2a,2b-dihomo" compounds, respectively, as discussed above.

When $Z_1$ is cis—CH$_2$—CH═CH—(CH$_2$)$_g$—CH$_2$—, wherein g is as defined above, the compounds so described are named "cis-4,5-didehydro-TXA$_1$" compounds. When g is 2 or 3, the compounds so described are further characterized as "2a-homo" or "2a,2b-dihomo" compounds, respectively, as discussed above.

When $Z_1$ is —(CH$_2$)$_2$—O—(CH$_2$)$_g$—CH$_2$, the compounds so described are named as "4-oxa-TXA$_1$" compounds. Similarly when $Z_1$ is trans—CH$_2$—(CH$_2$)$_g$—CH$_2$—CH═CH—, the compounds so described are "trans-2,3-didehydro-TXA$_1$" compounds.

The novel prostaglandin analogs herein which contain —(CH$_2$)$_2$—, cis—CH═CH—, or —C≡C— as the $Y_1$ moiety, are accordingly referred to as "13,14-dihydro", "cis-13", or "13,14-didehydro" compounds, respectively.

When $R_7$ is —(CH$_2$)$_m$—CH$_3$, wherein m is as defined above, the compounds so described are named as "19,20-dinor", "20-nor", "20-methyl" or "20-methyl" compounds when m is one, 2, 4, or 5, respectively.

When $R_7$ is phenyl and neither $R_3$ nor $R_4$ is methyl, the compounds so described are named as "16-phenyl-17,18,19,20-tetranor" compounds, when s is zero. When $R_7$ is substituted phenyl, the corresponding compounds are named as "16-(substituted phenyl)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-phenyl-16-phenyl or 16-(substituted phenyl)-18,19,20-trinor" compounds, respectively.

When $R_7$ is phenylmethyl, the compounds so described are named as "17-phenyl-18,19,20-trinor" compounds. When $R_7$ is substituted phenylmethyl the corresponding compounds are named as "17-(substituted phenyl)-18,19,20-trinor" compounds.

When $R_7$ is phenylethyl the compounds so described are named as "18-phenyl-19,20-dinor" compounds, when s is 0. When s is one, 2, or 3, the corresponding compounds are named as "18-(substituted phenyl)-19,20-dinor" compounds.

When $R_7$ is phenylpropyl, the compounds so described are named as "19-phenyl-20-nor" compounds. When $R_7$ is substituted phenylpropyl the corresponding compounds are named as "19-(substituted phenyl)-20-nor" compounds.

When $R_7$ is phenoxy and neither $R_3$ nor $R_4$ is methyl, the compounds so described are named as "16-phenoxy-17,18,19,20-tetranor" compounds. When $R_7$ is substituted phenoxy the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —CH$_2$OH, the compounds so described are named as "2-decarboxy-2-hydroxymethyl" compounds.

When $X_1$ is —CH$_2$NL$_2$L$_3$, the compounds so described are named as "2-decarboxy-2-aminomethyl" or "2-(substituted amino)methyl" compounds.

When $X_1$ is —COL$_4$, the novel compounds herein are named as TXA-type, amides. Further, when $X_1$ is —COOR$_1$, the novel compounds herein are named as TXA-type, esters and TXA-type, salts.

Examples of phenyl esters substituted in the para position (i.e., $X_1$ is —COOR$_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-carboxyphenyl ester, p-amidocarbonylaminophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)-phenyl ester, and p-hydroxybenzaldehyde semicarbazone ester.

Examples of novel amides herein (i.e., $X_1$ is —COL$_4$) include the following:

(1) Amides within the scope of alkylamino groups of the formlula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, 2-phenylethylamide, and N-methyl-N-benzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are
p-chlorobenzoylmethylamide, m-chlorobenzoylmethylamide,
2,4-dichlorobenzoylmethylamide,
2,4,6-trichlorobenzoylmethylamide,
m-nitrobenzoylmethylamide, p-nitrobenzoylmethylamide,
p-methoxybenzoylmethylamide,
2,4-dimethoxybenzoylmethylamide,
3,4,5-trimethoxybenzoylmethylamide,
p-hydroxymethylbenzoylmethylamide,
p-methylbenzoylmethylamide, m-methylbenzoylmethylamide,
p-ethylbenzoylmethylamide, t-butylbenzoylmethylamide,
p-carboxybenzoylmethylamide,
m-methoxycarbonylbenzoylmethylamide,
o-carboxybenzoylmethylamide, o-hydroxybenzoylmethylamide,
p-chlorobenzoylethylamide, m-chlorobenzoylethylamide,
2,4-dichlorobenzoylethylamide,
2,4,6-trichlorobenzoylethylamide,
m-nitrobenzoylethylamide, p-nitrobenzoylethylamide,
p-methoxybenzoylethylamide, p-methoxybenzoylethylamide,
2,4-dimethoxybenzoylethylamide,
3,4,5-trimethoxybenzoylethylamide,
p-hydroxymethylbenzoylethylamide,
p-methylbenzoylethylamide, m-methylbenzoylethylamide,
p-ethylbenzoylethylamide, t-butylbenzoylethylamide,
p-carboxybenzoylethylamide,
m-methoxycarbonylbenzoylethylamide,
o-carboxybenzoylethylamide, o-hydroxybenzoylethylamide,
p-chlorobenzoylpropylamide, m-chlorobenzoylpropylamide,
2,4-dichlorobenzoylpropylamide,
2,4,6-trichlroobenzoylpropylamide,
m-nitrobenzoylpropylamide, p-nitrobenzoylpropylamide,
p-methoxybenzoylpropylamide,
2,4-dimethoxybenzoylpropylamide,
3,4,5-trimethoxybenzoylpropylamide,
p-hydroxymethylbenzoylpropylamide,
p-methylbenzoylpropylamide, m-methylbenzoylpropylamide,
p-ethylbenzoylpropylamide, t-butylbenzoylpropylamide,
p-carboxybenzoylpropylamide,
m-methoxycarbonylbenzoylpropylamide,
o-carboxybenzoylpropylamide, o-hydroxybenzoylpropylamide,
p-chlorobenzoylbutylamide, m-chlorobenzoylbutylamide,
2,4-dichlorobenzoylbutylamide,
2,4,6-trichlorobenzoylbutylamide,
m-nitrobenzoylbutylamide, p-nitrobenzoylbutylamide,
p-methoxybenzoylbutylamide,
2,4-dimethoxybenzoylbutylamide,
3,4,5-trimethoxybenzoylbutylamide,
p-hydroxymethylbenzoylbutylamide,
p-methylbenzoylbutylamide, m-methylbenzoylbutylamide,
p-ethylbenzoylbutylamide, m-methylbenzoylbutylamide,
p-ethylbenzoylbutylamide, t-butylbenzoylbutylamide,
p-carboxybenzoylbutylamide,
m-methoxycarbonylbenzoylbutylamide,
o-carboxybenzoylbutylamide, o-hydroxybenzoylmethylamide.

Amides within the scope of pyridylamino are
α-pyridylamide; β-pyridylamide, and γ-pyridylamide.
Amides within the scope of substituted pyridylamino are
4-methyl-α-pyridylamide, 4-methyl-β-pyridylamide,
4-chloro-α-pyridylamide, and 4-chloro-β-pyridylamide.
Amides within the scope of pyridylalkylamino are
α-pyridylmethylamide, β-pyridylmethylamide,
γ-pyridylmethylamide, α-pyridylethylamide,
β-pyridylethylamide, γ-pyridylethylamide,
α-pyridylpropylamide, β-pyridylpropylamide,
γ-pyridylpropylamide, α-pyridylbutylamide,
β-pyridylbutylamide, and γ-pyridylbutylamide.
Amides within the scope of substituted pyridylalkylamido are
4-methyl-α-pyridylmethylamide,
4-methyl-β-pyridylmethylamide,
4-chloro-α-pyridylmethylamide,
4-chloro-β-pyridylmethylamide,
4-methyl-α-pyridylpropylamide,
4-methyl-β-pyridylpropylamide,
4-chloro-α-pyridylpropylamide,
4-chloro-β-pyridylpropylamide,
4-methyl-α-pyridylbutylamide,
4-methyl-β-pyridylbutylamide,
4-chloro-α-pyridylbutylamide,
4-chloro-β-pyridylbutylamide,
4-methyl-β-pyridylbutylamide.

Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide.

Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)-2-hydroxymethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-didihydroxybutylamide, δ,δ-dihydroxybutylamide, and 1,1-bis(hydroxymethyl)ethylamide.

Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{23}COR_{21}$ are methylcarbonylamide, ethylcarbonylamide, phenylcarbonylamide, and benzylcarbonylamide.

(4) Amides within the scope of sulfonylamino of the formula $-NR_{23}SO_2R_{21}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-napthylethyl), and 1-(2-napthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of substituted phenoxy, phenylmethyl, phenylethyl, or phenylpropyl of the $R_7$ moiety are (o-, m-, or p-)tolyl, (o-, m-, or p-(ethylphenyl, 2-ethyltolyl, 4-ethyl-o-tolyl, 5-ethyl-m-tolyl, (o-, m-, or p-(propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 2-ethyltolyloxy, 4-ethyl-o-tolyloxy, 5-ethyl-m-tolyloxy, (o-, m-, or p-)propylphenoxy, 2-propyl-(o-, m-, or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-dluoro-(o-, m-, or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3,4,5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenoxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenylmethyl, 2-ethyltolylmethyl, 4-ethyl-o-tolylmethyl, 5-ethyl-m-tolylmethyl, (o-, m-, or p-)propylphenylmethyl, 2-propyl-(o-, m-, or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(o-, m-, or p-)tolylmethyl, 4-fluoro-2,5-xylylmethyl, (2,4-, 2,5-, 2,6-, 3,4-, or 3,5-)difluorophenyl, (o-, m-, or p-)chlorophenylmethyl, 2-chloro-p-tolylmethyl, (3,4,5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl.

The novel TXA analogs of this invention are highly active as inhibitors of the thromboxane synthetase enzyme system. Accordingly, these novel compounds are useful for administration to mammals, including humans, whenever it is desirable for medical or veterinary purposes to inhibit this enzyme system. For example, these novel compounds are useful as anti-inflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

The novel TXA analogs of this invention are useful in the treatment of asthma, are useful, for example, as bronchodilators or as inhibitors of mediators, such as SRS-A and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositores, parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use these compounds can be combined advantageously with other anti-asthmatic agents, such as sympathomimetics (isopropterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

These TXA analogs are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range of about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for tansplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animals, to the perfused body portion, attached or detached, to the recipient, or to two or all of those at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

When $X_1$ is —$COOR_1$, the novel TXA analogs so described are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When $X_1$ is —$CH_2NL_2L_3$, the novel TXA analogs so described are used for the purposes described above in either free base or pharmacologically acceptable acid addition salt form.

The acid addition salts of the 2-decarboxy-2-aminomethyl- or 2-(substituted aminomethyl)-TXA analogs provided by this invention, are the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the TXA analog with the stoichiometric amount of the acid corresponding to the pharmacologically acceptable acid addition salt.

To obtain the optimum combination of biological response specificity, potency, and duration of activity, certain compounds within the scope of this invention are preferred.

It is preferred that in the 8α-side chain g be either one or 3, especially one, i.e., the natural chain length of TXA$_2$. Further when the C-12 side chain contains —(CH$_2$)$_m$—CH$_3$, it is preferred that m be 3 or 4, most preferably 3. Further, it is preferred that, when R$_7$ is aromatic, R$_7$ be phenoxy, phenyl, or phenylmethyl, including substituted forms thereof. For those compounds wherein R$_7$ is substituted phenoxy or phenylalkyl, it is preferred there be only one or two substituents selected from the group consisting of chloro, fluoro, or trifluoromethyl. Further, for those compounds wherein R$_7$ is aromatic, it is preferred that R$_3$ and R$_4$ both be hydrogen.

Finally preferred are those compounds wherein M$_1$ is α-H:β-H or where —C(M$_1$)—C(L$_1$) is trans—CH═CH—.

Especially preferred are those compounds which satisfy two or more of the above preferences. Further, the above preferences are expressly intended to describe the preferred compounds within the scope of any generic formula of novel prostaglandin analogs disclosed herein.

The Charts herein describe methods whereby the novel thromboxane analogs of this invention are prepared.

With respect to the Charts, L$_1$, L$_2$, L$_3$, M$_1$, M$_7$, R$_7$, R$_{12}$, and Y$_1$ are as defined above.

Those stable, acid hydrolyzable blocking groups within the scope of R$_{10}$ of the M$_7$ moiety are any group which replaces a hydroxy hydrogen and is neither attacked by nor as reactive to the reagents used in the transformations used herein as an hydroxy is and which is subsequently replaceable with hydrogen in the preparation of the prostaglandin-type compounds. Several blocking groups are known in the art, e.g., tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include:
(a) tetrahydropyranyl;
(b) tetrahydrofuranyl;
(c) —C(OR$_{21}$)(R$_{22}$)-CH(R$_{23}$)(R$_{24}$), and
(d) —SiR$_{25}$R$_{26}$R$_{27}$,
wherein R$_{21}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, and wherein R$_{22}$ and R$_{23}$ are alkyl of 1 to 4 carbon atoms, inclusive, phenyl, phenyl substituted with 1, 2, or 3 alkyl of one to 4 carbon atoms, inclusive, or when R$_{22}$ and R$_{23}$ are taken together —(CH$_2$)$_a$— or —(CH$_2$)$_b$—O—(CH$_2$)$_c$—, wherein a is 3, 4, or 5, or b is 1, 2, or 3, and c is 1, 2, or 3, with the proviso that b plus c is 2, 3, or 4, with the further proviso that R$_{22}$ and R$_{23}$ may be the same or different, wherein R$_{24}$ is hydrogen or phenyl; and wherein R$_{25}$, R$_{26}$, and R$_{27}$ are alkyl of one to 18 carbon atoms, inclusive, cycloalkyl of 3 to 10 carbon atoms, inclusive, aralkyl of 7 to 12 carbon atoms, inclusive, phenyl, or phenyl substituted with one to 3 alkyl of one to 4 carbon atoms, inclusive, being the same or different with at least one of R$_{25}$ R$_{26}$, and R$_{27}$ preferably being tertiary alkyl (most preferably t-butyl).

When the stable, acid hydrolyzable blocking group R$_{10}$ is tetrahydropyranyl, the tetrahydropyranyl ether derivative of the hydroxy of the TXB-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

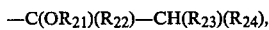

wherein R$_{21}$, R$_{22}$, R$_{23}$, and R$_{24}$ are as defined above, the appropriate reagent is a vinyl ether, e.g., isobutyl vinyl ether or any vinyl ether of the formula C(OR$_{21}$)(R$_{22}$)═C(R$_{23}$)(R$_{24}$), or an unsaturated cyclic or heterocyclic compound, e.g., 1-cyclohexen-1-yl methyl ether, or 4,5-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above. Finally, when the stable, acid hydrolyzable group is silyl, methods of preparation are those known in the art; see Pierce, "Silylation of Organic Compounds", Pierce Chemical Co., Rockford, Ill. (1968).

The blocking groups according to R$_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperature below 55° C., hydrolysis of the blocking groups is achieved. Optionally the silyl groups are removed by the methods of Corey, E.G., et al., JACS 94:6190 (1972), i.e., tetra-n-butyl-ammonium fluoride in THF.

Finally R$_{28}$, R$_{29}$, and R$_{30}$ of Chart A are as defined above for R$_{12}$, being the same or different, but especially are all methyl.

Chart A provides a method whereby the formula XXI PGA-type compound is transformed to the formula XXX 11a-homo-11β-PGFα-type intermediate. With respect to Chart A, the formula XXI compounds are known in the art or prepared by methods known in the art. For example, these formula XXI PGA-type compounds are prepared by acidic dehydration of the corresponding PGE-type compounds, or prepared from the corresponding PGF-type, 11,15-bis ethers by oxidation, followed by acidic dehydration.

The formula XXII silylcyanohydrin is prepared from the formula XXI compound by reaction with the appropriate silyl cyanide, i.e., R$_{28}$, R$_{29}$, R$_{30}$, SiC≡N in the presence of a cyanide-crown ether catalyst, preferably a catalyst consisting of potassium cyanide and 18-crown-6 ether. See Pedersen, J. C., JACS 92:386 (1970) for a description of the preparations and use of the crown ethers.

The formula XXII compound thusly prepared is thereafter reduced, preferably with lithium aluminum hydride, to prepare the formula XXIII amine corresponding to the corresponding formula XXII compound. Thereafter, this formula XXIII compound is transformed to the formula XXIV 2-decarboxy-2-hydroxymethyl-9a-homo-PGA-type compound employing a Tiffeneau-Demjanov ring expansion. See Evans, D. A., et al., J. Org. Chem. 59:914 (1974) and Smith, P. A. S., et al., Organic Reactions, Vol XI, p. 157 (1960). The formula XXIV compound is then isomerized to the formula XXV 2-decarboxy-2-hydroxymethyl-11a-homo-PGA-type compound by prolonged treatment under mild basic conditions, e.g., treatment with basic alumina in an organic solvent.

Thereafter the formula XXV compound is oxidized to the corresponding formula XXVI carboxylic acid by conventional means, e.g., Jones reagent. This formula XXVI 11a-homo-PGA-type compound is then transformed to the corresponding formula XXVII ester by conventional means, e.g., ethereal diazoalkanes or alkyl iodides.

Thereafter, the formula XXVII 11a-homo-PGA-type compound is epoxidized to the formula XXVIII compound and thereafter reduced to the formula XXIX 11a-homo-11$\beta$-PGE-type compound. Epoxidation and reduction methods employed are those known in the art for the preparation of the corresponding 11$\beta$-PGE compounds from the corresponding PGA compounds. See U.S. Pat. No. 3,904,657, issued Sept. 9, 1975. Finally in Chart A, the formula XXIX compound is reduced to the corresponding 11a-homo-11$\beta$-PGF$_\alpha$-type formula XXX compound by conventional means. Especially useful reducing agents for this purpose are the tri-sec-butylborohydride reducing agents, e.g., lithium tri-sec-butylborohydride.

Chart B provides a method whereby the formula XXXI compound (the ultimate product from Chart A) is transformed to the novel formula XXXII, formula XXXIII, and formula XXXV thromboxane analogs.

With respect to Chart B the formula XXXI compound is transformed to either the formula XXXIII compound or a mixture of the formula XXXIII and formula XXXIII compounds. The latter mixture is obtained when $M_7$ is not $\alpha$-H:$\beta$-H and $R_3$, $R_4$, and $R_5$ are all hydrogen. When such mixture of products is obtained, it is conveniently separated by chromatographic techniques, e.g., column chromatography employing silica gel.

The transformation of the formula XXXI compound to either the formula XXXIII or a mixture of the formula XXXII and XXXIII compounds proceeds by cyclization employing trifluoromethanesulfonic anhydride. This epoxidation reaction proceeds by placing the formula XXXI compound in an organic solvent and cooling to about $-78°$ C. to $-130°$ C. Thereupon the trifluoromethanesulfonic anhydride in organic solvent is added. When silica gel TLC indicates the reaction to be complete, the desired product or products are recovered by conventional means.

Alternatively, the formula XXXI compound wherein $M_7$ is not $\alpha$-H:$\beta$-H and $R_5$ is hydrogen is deoxygenated at C-15 to the formula XXXIV compound. Methods for this deoxygenation are those known in the art, e.g., those employed in the production of 15-deoxy-azo- and epoxyiminoprostaglandin-type compounds. See U.S. Pat. No. 4,122,224 for a description of these means. Thereafter, the formula XXXIV compound is cyclized to the formula XXXV compound by the methods described for the cyclization of the formula XXXI compound to the formulas XXXII and XXXIII products.

Finally, Chart C describes the methods whereby the novel thromboxane analogs in ester form are transformed to the corresponding free acid, primary alcohol, amide, amine or other ester form. With respect to Chart C, the formula XLI ester is saponified to the corresponding formula XLII carboxylic acid by methods known in the art for the saponification of prostaglandin analogs to their corresponding carboxylic acids. Alternatively, the formula XLI compound is reduced to the corresponding primary alcohol by methods known in the art, e.g., lithium aluminum hydride reduction, preferably at temperatures below about $-20°$ C. See U.S. Pat. No. 4,028,419, issued 7 June 1977.

The formula XLII compound is transformed to the corresponding formula XLIV amide by amidization methods known in the art for prostaglandin analogs. See especially U.S. Pat. No. 4,100,192, issued 11 July 1978, for a description of these methods. This formula XLIV product may then be reduced to the corresponding amine (the formula XLV compound) by reduction, e.g., with lithium aluminum hydride, or by other amination methods described in U.S. Pat. No. 4,081,478, issued 28 March 1978.

Finally, the formula XLII compound is transformed to the formula XLVI esters by esterification methods known in the art.

Accordingly, the various compounds in accordance with the present invention are all prepared by the methods and charts above.

DESCRIPTION OF THE PREFERRED EMBODIMENTS

The present invention is more fully understood by the following examples:

EXAMPLE 1

11a-homo-11$\beta$-PGF$_{2\alpha}$, methyl ester, 15(t-butyldimethylsilyl) ether (Formula XXX: $R_{12}$ is methyl, $Z_1$ is Cis—CH=CH—(H$_2$)$_3$, $Y_1$ is trans—CH=CH—, $M_1$ is $\alpha$-t-butyldimethylsilyloxy: $\beta$-hydrogen, $R_3$ and $R_4$ of the $L_1$ moiety are both hydrogen and $R_7$ is n-butyl).

Refer to Chart A.

A. PGA$_2$, methyl ester, trimethylsilylcyanohydrin, 15-(t-butyldimethylsilyl) ether (Formula XXII: $R_{28}$, $R_{29}$, and $R_{30}$ are all methyl, and $R_{12}$, $Z_1$, $Y_1$, $M_7$, $L_1$, and $R_7$ are as defined for the title product).

PGA$_2$, methyl ester, 15-(t-butyldimethylsilyl) ether (10 g) is combined with chloroform (200 ml) previously passed through 50 g of neutral alumina in a column. Crystalline neopentyl alcohol (0.5 g) is added, followed by addition of trimethylsilyl cyanide (4 ml) and 200 mg of a potassium cyanide-18-crown-6 ether catalyst. The catalyst is prepared by dissolving equivalent amounts of potassium cyanide and 18-crown-6 ether (Catalog Handbook of Fine Chemicals 1979–1980, Aldrich Chemical Co., Milwaukee, Wis., page 133; see also Pedersen, J. C., JACS 92:386 (1970)) in methanol and evaporation of the solvent to dryness. The resulting reaction mixture is then stirred under a nitrogen atmosphere, filtered under vacuum suction through silica gel (1 kg) packed in ethyl acetate. Elution with ethyl acetate (1 liter) yields two 500 ml fractions, the first of which contains 1 g of PGA$_2$, methyl ester, trimethylsilylcyanohydrin, 15-(t-butyldimethylsilyl) ether. NMR absorptions are observed at 0.25, 0.91, 0.9–2.6, 3.68, 4.1, 6.0–5.25, 5.85, and 5.45$\delta$. Characteristic infrared absorptions are observed at 2880, 2220, 1735, 1440, 1360, 1240, 1140, 1080, 960, 845, and 770 cm$^{-1}$. Silica gel TLC R$_f$ is 0.75 in ethyl acetate and hexane (1:4). The mass spectrum exhibits a weak molecular ion at 561 and other peaks at 546, 530, and 504.

B. 2-Decarboxy-2-hydroxymethyl-9,11-dideoxy-9-hydroxy-9-aminomethyl-10,11-didehydro-PGF$_2$, 15-(t-butyldimethylsilyl) ether (Formula XXIII: Y$_1$, M$_7$, L$_1$, and R$_7$ are as defined for the title product).

A solution of 11.4 g of the reaction product of Part A in 500 ml of dry tetrahydrofuran is cooled to 0° C. and 5 g of lithium aluminum hydride is added with stirring, the rate of addition being such that tetrahydrofuran is below reflux temperature. Once addition is complete, the reaction is allowed to warm to 25° C., stirred for an additional 2 hr., and quenched by addition of water (10 ml) and 10% aqueous sodium hydroxide (8 ml). The resulting grey slurry is then stirred overnight and the aluminum salts removed by filtration. The resulting solution is then dried over magnesium sulfate and concentrated under reduced pressure to yield 9.71 g of product as a white oil. NMR absorptions are observed at 0.2, 0.90, 0.9–2.5, 2.6, 3.6, and 5.9–5.0δ. Infrared absorptions are observed at 3250, 2880, 1440, 1340, 1240, 1080, 955, 830, and 770 cm$^{-1}$.

C. 2-Decarboxy-2-hydroxymethyl-9a-homo-PGA$_2$, 15-(t-butyldimethylsilyl) ether (Formula XXIV: Z$_1$, Y$_1$, M$_7$, L$_1$, and R$_7$ are as defined for the title product).

The reaction product of Part B (1.52 g) is dissolved in a mixture of water (15 ml) and acetic acid (2 ml). While stirring at 25° C., nitrous acid (generated by the addition of 300 mg of crystalline sodium nitrite) is added and the resulting mixture stirred vigorously. After evolution of nitrogen gas ceases (about 1 hr) the reaction mixture is extracted with ethyl acetate and the organic layer washed successively with saturated sodium bicarbonate and brine, dried over sodium sulfate, and concentrated under reduced pressure to an oil. Chromatographing on 70 g of silica gel packed and eluted with 30% ethyl acetate in hexane yields 480 mg of product. NMR absorptions are observed at 0.2, 1.0–3.0, 3.6–3.75, 4.1, and 5.1–5.9δ. IR absorptions are observed at 3450, 2880, 2800, 1705, 1440, 1240, 1060, 960, 830, and 770 L cm$^{-1}$. Silica gel TLC R$_f$ is 0.32 in 30% ethyl acetate and hexane. The mass spectrum exhibits a weak molecular ion at 520, a high resolution demethylated molecular ion at 505.509 and other peaks at 463, 449, 338, 436, and 215.

D. 2-Decarboxy-2-hydroxymethyl-11a-homo-PGA$_2$ 15-(t-butyldimethylsilyl) ether. (Formula XXV: Z$_1$, Y$_1$, M$_7$, L$_1$, and R$_7$ are as defined for the title product).

The reaction product of Part C (2.8 g) is dissolved in 20 ml of tetrahydrofuran and 15 g of basic alumina is added with vigorous stirring. After 18 hr the reaction mixture is extracted with ethyl acetate and the solvent evaporated to dryness yielding the desired product. NMR absorptions are observed at 0.1, 0.9, 1.0–2.6, 3.7–3.5, 4.1, 5.5–5.0, 7.2–6.8, and 6.1–5.8δ. Infrared absorptions are observed at 3450, 2920, 1670, 1240, 1030, 830, and 770 cm$^{-1}$. Silica gel TLC R$_f$ is 0.28 in ethyl acetate and hexane (3:7). The mass spectrum exhibits a molecular ion at 520, a high resolution peak (demethylated molecular ion) at 505.3520 and other peaks at 463, 449, 388, and 373.

E. 11a-homo-PGA$_2$ 15-(t-butyldimethylsilyl) ether. (Formula XXVI Z$_1$, Y$_1$, M$_7$, L$_1$, and R$_7$ are as defined for the title product).

The reaction product of Part D (2.4 g) and 200 ml of acetone is cooled to −20° C. in a saline ice bath. Jones reagent (1.6 ml) is added and the resulting mixture stirred at −20° C. under a nitrogen atmosphere. After 4 hr, additional Jones reagent (2 ml) is added and the resulting mixture stirred for an additional hour. Thereupon the resulting mixture is poured into 200 ml of ice and water, extracted with ethyl acetate, and the organic layers successively washed with water and brine. The organic phase is then dried over sodium sulfate and concentrated under reduced pressure to dryness yielding product. Silica gel TLC R$_f$ is 0.36 in ethyl acetate and hexane (3:7) containing 1% acetic acid.

F. 11a-homo-PGA$_2$, methyl ester 15-(t-butyldimethylsilyl) ether. (Formula XXVII)

The product of Part E (2.4 g) is dissolved in 50 ml of acetonitrile and the resulting solution stirred at ambient temperature under a nitrogen atmosphere. Thereupon ethyl diisopropylamine (3.2 ml) and methyl iodide (6.4 ml) are added. After about 1 hr, the resulting mixture is poured into brine, ice, and potassium bisulfate (2 M) and extracted with ethyl acetate. The organic layer is then washed with brine, concentrated under reduced pressure, and the residue chromatographed on silica gel (250 g) packed and eluted with 20% ethyl acetate in hexane. The product is thereby obtained (938 mg) as an oil. Silica gel TLC R$_f$ is 0.57 in ethyl acetate and hexane (3:7). The mass spectrum exhibits a high resolution peak (demethylated molecular ion) at 461.3099 and other peaks at 445, 419, 344, and 215.

G. 11-Deoxy-11a-homo-10β,11β-epoxy-PGE$_2$, methyl ester, 15-(t-butyldimethylsilyl) ether (Formula XXVIII: R$_{12}$, Z$_1$, Y$_1$, M$_7$, L$_1$, and R$_7$ are as defined for the title product).

The reaction product of Part F (868 mg) is dissolved in 20 ml of methanol and the resulting solution cooled to 20° C. Thereupon 30% aqueous hydrogen peroxide (0.99 ml) is added, followed by addition of 0.12 ml of 1 M aqueous potassium hydroxide. After 18 hr at −20° C., the reaction mixture is then diluted with ethyl acetate and the organic layer is washed with brine, dried over sodium sulfate, and concentrated under reduced pressure. The residue is then chromatographed on 100 g of silica gel packed and eluted with ethyl acetate and hexane (1:9) to yield 262 mg of pure product. Later fractions yield 458 mg of the corresponding 9α,11α-isomer. Infrared absorptions are observed at 2940, 2800, 1740, 1720, 1420, 1220, 1040, 830, and 770 cm$^{-1}$. The mass spectrum exhibits peaks at 461, 435, and 421.

H. 11a-Homo-11β-PGE$_2$, methyl ester 15-(t-butyldimethylsilyl) ether. (Formula XXIX: R$_{12}$, Z$_1$, Y$_1$, M$_7$, L$_1$, and R$_7$ are as defined for the title product).

The reaction product of Part G (2.0 g) is dissolved in 100 ml of a mixture of diethyl ether, methanol, and water (100:10:1) and treated with 4 g of aluminum amalgum (prepared from 4 g of aluminum and 4 g of mercuric chloride) and the resulting mixture allowed to stir at ambient temperature for 4 hr. Thereafter the resulting solution is filtered through a pad of diatomaceous earth and the solvent removed by evaporation. The resulting oil so obtained is then chromatographed on 150 g of silica gel packed and eluted with 40% ethyl acetate in hexane yielding 1.52 g of product. Silica gel TLC R$_f$ is 0.21 in ethyl acetate and hexane (3:7).

I. 11a-Homo-11β-PGF$_{2\alpha}$, methyl ester 15-(t-butyldimethylsilyl) ether.

The reaction product of Part H (466 mg) is dissolved in 20 ml of dry tetrahydrofuran and cooled to −78° C. in dry ice and acetone. The solution is then treated with 1.0 ml of a 1 M solution of lithium tri-sec-butylborohydride and maintained at −78° C. for 2 hr. After warming to ambient temperature 3 ml of water, 1 ml of 30% aqueous hydrogen peroxide and 0.5 ml of 1 M aqueous potassium hydroxide are added. The resulting mixture is then maintained at ambient temperature for 1 hr, washed with brine, and the organic extracts dried over sodium sulfate and concentrated under reduced pressure. The oil thusly obtained is then chromatographed on 50 g of silica gel packed and eluted with ethyl acetate in hexane (2:3) yielding 350 mg of title product. Infrared absorptions are observed at 3450, 2950, 1740, 1480, 1245, 970, 840, and 977 cm$^{-1}$.

Following the procedure of Example 1, each of the various PGA-type compounds of formula XXI is transformed to the corresponding 11a-homo-11$\beta$-PGF$_\alpha$-type compound of formula XXX.

EXAMPLE 2

11a-Methano-TXA$_2$, methyl ester and 11a-Methano-15,16-didehydro-15-deoxy-TXA$_2$, methyl ester (Formulas XXIII and XXII, respectively: $R_{12}$, $Z_1$, $Y_1$, $L_1$, and $R_7$ are as defined in Example 1 and $M_1$ of formula XXXIII is $\alpha$-hydroxy:$\beta$-hydrogen).

Refer to Chart B.

The title product of Example 1 (100 mg) is dissolved in 5 ml of dry methylene chloride. Thereafter 1.2 equivalents of pyridine (19.5 $\mu$l) are added and the resulting solution cooled to $-120°$ C. in isooctane and liquid nitrogen. A solution of 37.3 $\mu$l of trifluoromethanesulfonic anhydride in 2 ml of dry methylene chloride is then added over 20 min. After 1.5 hr the resulting mixture is warmed to ambient temperature and washed with brine and aqueous sodium bicarbonate. The resulting solution is then extracted with ethyl acetate, washed with brine, dried over sodium sulfate, and concentrated to a light yellow oil. This oil is then chromatographed on 20 g of silica gel packed and eluted with ethyl acetate and hexane (1:9) and yields 14 mg of 11a-methano-TXA$_2$, methyl ester, and 25 mg of 11a-methano-15,16-didehydro-15-deoxy-TXA$_2$, methyl ester. For the former product silica gel TLC R$_f$ is 0.64 in ethyl acetate and hexane (3:7). Infrared absorptions are observed at 2975, 1738, 1435, 1385, 1310, 1240, 1150, 1040, 1020, 995, 970, 920, 800, and 700 cm$^{-1}$. NMR absorptions are observed at 0.9–2.5, 3.70, 4.1, 4.14–4.6, and 5.3–6.0$\delta$. The mass spectrum exhibits high resolution molecular ion at 346.2517 and other peaks are observed at 315, 220, and 188. For the latter product silica gel TLC R$_f$ is 0.15 in ethyl acetate and hexane (3:7). Infrared absorptions are observed at 3400, 2840, 1735, 1440, 1080, 995, 970, and 700 cm$^{-1}$. NMR absorptions are observed at 0.9–2.5, 3.65, 4.0–4.15, 4.15–4.25, 4.4–4.5, and 5.25–5.75$\delta$.

Following the procedure of Example 2, but employing each of the formula XXXI 11a-homo-11$\beta$-PGF$_\alpha$-type esters in place of 11a-homo-11$\beta$-PGF$_{2\alpha}$, methyl ester, there are prepared each of the various corresponding formula XXXII and XXXIII products.

EXAMPLE 3

11a-Methano-15-deoxy-TXA$_2$, methyl ester (Formula XXXV: $R_{12}$, $Z_1$, $Y_1$, $L_1$, and $R_7$ are as defined in Example 1).

Refer to Chart B.

A. The title product of Example 1 (1.0 g) and 22 ml of methanol is treated with 15 ml of 10% aqueous potassium hydroxide. After 48 hr, the methanol is evaporated under reduced pressure and the residue partitioned between hexane and ice cold 2 N sodium bisulfate and brine. The aqueous layers are then extracted with hexane and the combined organic extracts are then washed twice with brine, dried over sodium sulfate, and concentrated under reduced pressure to yield a free acid corresponding to the starting material, i.e., 11a-homo-11$\beta$-PGF$_{2\alpha}$, 15-(t-butyldimethylsilyl) ether.

B. Methylamine (15 ml) is condensed and maintained at $-30°$ to $-40°$ C. while 0.94 g of the reaction product of Part A in 2 ml of a mixture of t-butanol and tetrahydrofuran (1:10) is added. Thereupon 3 small pieces of lithium metal (approximately one third of a cm long) are added at the rate of one per min. After 10 min a deep blue color persists. After 30 min, 10.0 g of solid ammonium chloride are added and the solution becomes colorless. Methylamine is then allowed to evaporate at ambient temperature under a stream of nitrogen. Thereafter ice cold 2 N aqueous sodium bisulfate is added and the resulting mixture extracted with 10% ethyl acetate in hexane. The combined organic extracts are then washed twice with brine, dried over sodium sulfate, and concentrated under reduced pressure to yield the free acid corresponding to the formula XXXIV compound: 11a-homo-15-deoxy-11$\beta$-PGF$_{2\alpha}$.

C. The reaction product of Part B is then dissolved in 25 ml of acetonitrile and treated with 2 ml of diisopropylethylamine and 1 ml of methyl iodide an ambient temperature under a nitrogen atmosphere. After 3 hr the resulting mixture is then poured into brine and extracted with ethyl acetate. The combined organic extracts are then washed with brine, dried over sodium sulfate, and concentrated. The resulting product is then chromatographed on 75 g of silica gel yielding the formula XXXIV compound, 11a-homo-15-deoxy-11$\beta$-PGF$_{2\alpha}$, methyl ester.

D. Following the procedure of Example 2, the product of Part C of this example is cyclized to the formula XXXV title product.

Following the procedure of Example 3, there are prepared from each of the various formula XXXI compounds described following Example 1 each of the various formula XXXV 11a-methano-15-deoxy-TXA-type products.

EXAMPLE 4

11a-Methano-TXA$_2$ (Formula XLII: $Z_1$, $Y_1$, $M_1$, $L_1$, and $R_7$ are as defined in Example 2).

Refer to Chart C.

11a-Methano-TXA$_2$, methyl ester (20 mg) is dissolved in 1 ml of a mixture of tetrahydrofuran and water (2:1) and the resulting solution treated with 1 ml of 0.45 N lithium hydroxide at ambient temperature under a nitrogen atmosphere. After 3 hr of stirring, the resulting mixture is poured into 2 M aqueous potassium bisulfate, extracted with ethyl acetate, washed with brine, dried over sodium sulfate, and chromatographed on 10 g of acid-washed silica gel packed and eluted with 50% ethyl acetate in hexane.

Title product (17.3 mg) is thereby obtained. Silica gel TLC R$_f$ is 0.4 in ethyl acetate and hexane (1:1) containing 5% acetic acid. NMR absorptions are observed at 0.9–2.5, 4.0–4.18, 4.15–4.30, 4.35–4.5, and 4.9–5.0$\delta$.

EXAMPLE 5

11a-Methano-15,16-didehydro-15-deoxy-TXA$_2$ (Formula XLII: $Z_1$, $Y_1$, and $R_7$ are as defined in Example 2 and —C($M_1$)—C($L_1$)— is trans—CH=CH—).

Refer to Chart C.

Following the procedure of Example 4, 20 mg of 11a-methano-15,16-didehydro-15-deoxy-TXA$_2$, methyl ester is transformed to 12.5 mg of title product. Silica gel TLC $R_f$ is 0.41 in ethyl acetate and hexane (3:7) containing 5% acetic acid.

Following the procedure of Examples 4 and 5, there are prepared each of the various 11a-methano-TXA$_2$ compounds of formula XLII from the corresponding formula XLI esters.

EXAMPLE 6

2-Decarboxy-2-hydroxymethyl-11a-methano-TXA$_2$ (Formula XLIII: $Z_1$, $Y_1$, $M_1$, $L_1$, and $R_7$ are as defined in Example 2).

Refer to Chart C.

11a-Methano-TXA$_2$, methyl ester (750 mg) is dissolved in 50 ml of diethyl ether and treated with 500 mg of lithium aluminum hydride at $-20°$ C. with stirring. When the starting material is completely consumed (as indicated by TLC analysis) 1 ml of water is added cautiously. Thereafter 0.8 ml of 10% aqueous sodium hydroxide is added and the resulting mixture allowed to stir for 12 hr. Thereupon magnesium sulfate is added with stirring and the stirred mixture is filtered through magnesium sulfate and evaporated to a residue. Chromatographic purification yields pure title product.

Following the procedure of Example 6, each of the various formula XLI 11a-methano-TXA$_2$-type esters is transformed to the corresponding formula XLIII 2-decarboxy-2-hydroxymethyl-11a-methano-TXA compound.

EXAMPLE 7

11a-Methano-TXA$_2$, amide (Formula XLIV: $Z_1$, $Y_1$, $M_1$, $L_1$, and $R_7$ are as defined in Example 2 and $L_4$ is $-NH_2$).

Refer to Chart C.

A solution of 300 mg of 11a-methano-TXA$_2$ and 8 ml of dry acetonitrile is cooled to $-10°$ C. under a nitrogen atmosphere. Thereupon 0.127 ml of triethylamine is added, followed by addition of 0.18 ml of isobutylchloroformate. After 10 min at $-5°$ C. an ammonia-saturated solution of 3 ml of acetonitrile is added in one portion. After 5 min at $-5°$ C., and 10 min at ambient temperature, the reaction mixture is diluted with ethyl acetate and partitioned with a mixture of brine and KH$_2$PO$_4$ (added to adjust pH to about 4.5). The resulting layers are separated and the aqueous phase extracted with ethyl acetate. The organic extract is then washed with brine, dried over sodium sulfate, and concentrated to yield 0.3 g of a residue. This residue is chromatographed on silica gel packed and eluted with ethyl acetate yielding pure title product.

Following the procedure of Example 7, there are prepared each of the various formula XLIV 11a-methano-TXA$_2$-type amides corresponding to the formula XLII carboxylic acids.

EXAMPLE 8

2-Decarboxy-2-aminomethyl-11a-methano-TXA$_2$ (Formula XLV: $Z_1$, $Y_1$, $L_1$, $M_1$, and $R_7$ are as defined in Example 2 and $L_2$ and $L_3$ are both hydrogen).

Refer to Chart C.

Lithium aluminum hydride (100 mg) in 5 ml of dry tetrahydrofuran under nitrogen is treated dropwise with the title product of Example 7. The resulting mixture is then stirred at $-10°$ to $0°$ C. for 48 hr or until TLC analysis indicates reaction is complete and thereafter 0.1 ml of water is added while cooling in an ice bath. Thereafter 0.1 ml of 15% aqueous sodium hydroxide and 0.3 ml of water is added. The resulting suspension is then filtered, dried over magnesium sulfate, washed with ethyl acetate, and evaporated to a residue of title product.

Following the procedure of Example 8, but employing each of the various formula XLIV 11a-methano-TXA$_2$-type amides described Example 7, there are prepared each of the various corresponding formula XLV 2-decarboxy-2-aminomethyl-11a-methano-TXA-type compounds.

Following the procedure of the above examples, but employing the appropriate starting material as described above, there are prepared.

11a-Methano-TXA$_2$-type compounds;
11a-Methano-15,16-didehydro-15-deoxy-TXA$_2$-type compounds; or
11a-Methano-15-deoxy-TXA$_2$-type compounds in free acid, ester, or amide form, or as corresponding 2-decarboxy-2-aminomethyl or 2-decarboxy-2-hydroxymethyl derivatives which exhibit the following side chain variations:

15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;

15-methyl-16-phenoxy-18,19,20-trinor-13,14-didehydro-;
16-methyl-16-phenoxy-18,19,20-trinor-13,14-didehydro-;
13,14-dihydro-;
15-methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
15-methyl-16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
cis-13-;
15-methyl-cis-13-;
16-methyl-cis-13-;
16,16-dimethyl-cis-13-;
16-fluoro-cis-13-;
16,16-difluoro-cis-13-;
15-methyl-16,16-difluoro-cis-13-;
17-phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-flurophenyl)-18,19,20-trinor-cis-13-;
15-methyl-17-phenyl-18,19,20-trinor-cis-13-;
16-methyl-17-phenyl-18,19,20-trinor-cis-13-;
16,16-dimethyl-17-phenyl-18,19,20-trinor-cis-13-;
16-fluoro-17-phenyl-18,19,20-trinor-cis-13-;
16,16-difluoro-17-phenyl-18,19,20-trinor-cis-13-;
15-methyl-16,16-difluoro-17-phenyl-18,19,20-trinor-cis-13-;
16-phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
15-methyl-16-phenoxy-17,18,19,20-tetranor-cis-13-;
16-phenoxy-18,19,20-trinor-cis-13-;
15-methyl-16-phenoxy-18,19,20-trinor-cis-13-;
16-methyl-16-phenoxy-18,19,20-trinor-cis-13-;
2,2-difluoro-;
2,2-difluoro-15-methyl-;
2,2-difluoro-16-methyl-;
2,2-difluoro-16,16-dimethyl-;
2,2,16-trifluoro-;
2,2,16,16-tetrafluoro-;
2,2,16,16-tetrafluoro-15-methyl-;
2,2-difluoro-17-phenyl-18,19,20-trinor-;
2,2-difluoro-15-methyl-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor-;
2,2-difluoro-16-methyl-17-phenyl-18,19,20-trinor-;
2,2-difluoro-16,16-dimethyl-17-phenyl-18,19,20-trinor-;
2,2-difluoro-16-fluoro-17-phenyl-18,19,20-trinor-;
2,2-difluoro-16,16-difluoro-17-phenyl-18,19,20-trinor-;
2,2-difluoro-15-methyl-16,16-difluoro-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-(p-fluorophenoxy)-17,18,19,20-tetranor-;
2,2-difluoro-15-methyl-16-phenoxy-17,18,19,20-tetranor-;
2,2-difluoro-16-phenoxy-18,19,20-trinor-;
2,2-difluoro-15-methyl-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2-difluoro-16-fluoro-13,14-didehydro-;
2,2-difluoro-16,16-difluoro-13,14-didehydro-;
2,2,16,16-tetrafluoro-15-methyl-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-difluoro-15-methyl-17-phenyl-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;
2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-15-methyl-16-phenoxy-17,18,19,20-tetranor-13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-15-methyl-13,14-dihydro-;
2,2-difluoro-16-methyl-13,14-dihydro-;
2,2-difluoro-16,16-dimethyl-13,14-dihydro-;
2,2,16-trifluoro-13,14-dihydro-;
2,2,16,16-tetrafluoro-13,14-dihydro-;

2,2,16,16-tetrafluoro-15-methyl-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-15-methyl-17-phenyl-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2,16-trifluoro-17-phenyl-18,19,20-dihydro-;
2,2,16,16-tetrafluoro-17-phenyl-18,19,20-dihydro-;
2,2-difluoro-16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy)-17,18,19,20-tetranor-13,14-dihydro-;
2,2-difluoro-15-methyl-16-phenoxy-17,18,19,20-tetranor-13,14-dihydro-;
2,2-difluoro-16-phenoxy-18,19,20-trinor-13,14-dihydro-;
2,2-difluoro-15-methyl-16-phenoxy-18,19,20-trinor-13,14-dihydro-;
2,2-difluoro-16-methyl-16-phenoxy-18,19,20-trinor-13,14-dihydro-;
2,2-difluoro-cis-13-;
2,2-difluoro-15-methyl-cis-13-;
2,2-difluoro-16-methyl-cis-13-;
2,2-difluoro-16,16-dimethyl-cis-13-;
2,2,16-trifluoro-cis-13-;
2,2,16,16-tetrafluoro-cis-13-;
2,2,16,16-tetrafluoro-15-methyl-cis-13-;
2,2-difluoro-17-phenyl-18,19,20-trinor-cis-13-;
2,2-difluoro-17-(m-trifluoromethylphenyl)-18,19,20-trinor-cis-13-;
2,2-difluoro-17-(m-chlorophenyl)-18,19,20-trinor-cis-13-;
2,2-difluoro-17-(p-fluorophenyl)-18,19,20-trinor-cis-13-;
2,2-difluoro-15-methyl-17-phenyl-18,19,20-trinor-cis-13-;
2,2-difluoro-16-methyl-17-phenyl-18,19,20-trinor-cis-13-;
2,2-difluoro-16,16-dimethyl-17-phenyl-18,19,20-trinor-cis-13-;
2,2,16-trifluoro-17-phenyl-18,19,20-trinor-cis-13-;
2,2,16,16-tetrafluoro-17-phenyl-18,19,20-trinor-cis-13-;
2,2,16,16-tetrafluoro-17-phenyl-18,19,20-trinor-cis-13-;
2,2-difluoro-16-phenoxy-17,18,19,20-tetranor-cis-13-;
2,2-difluoro-16-(m-trifluoromethylphenoxy)-17,18,19,20-tetranor-cis-13-;
2,2-difluoro-16-(m-chlorophenoxy)-17,18,19,20-tetranor-cis-13-;
2,2-difluoro-16-(p-fluorophenoxy)-17,18,19,20-tetranor-cis-13-;
2,2-difluoro-15-methyl-16-phenoxy-17,18,19,20-tetranor-cis-13-;
2,2-difluoro-16-phenoxy-18,19,20-trinor-cis-13-;
2,2-difluoro-15-methyl-16-phenoxy-18,19,20-trinor-cis-13-;
2,2-difluoro-16-methyl-16-phenoxy-18,19,20-trinor-cis-13-;

2a,2b-dihomo-16-methyl-;
2a,2b-dihomo-16,16-dimethyl-;
2a,2b-dihomo-16-fluoro-;
2a,2b-dihomo-16,16-difluoro-;
2a,2b-dihomo-15-methyl-16,16-difluoro-;
2a,2b-dihomo-17-phenyl-18,19,20-trinor-;
2a,2b-dihomo-17-(m-trifluoromethylphenyl)-18,19,20-trinor-;
2a,2b-dihomo-17-(m-chlorophenyl)-18,19,20-trinor-;
2a,2b-dihomo-17-(p-fluorophenyl)-18,19,20-trinor-;
2a,2b-dihomo-15-methyl-17-phenyl-18,19,20-trinor-;
2a,2b-dihomo-16-methyl-17-phenyl-18,19,20-trinor;
2a,2b-dihomo-16,16-dimethyl-17-phenyl-18,19,20-trinor-;
2a,2b-dihomo-16-fluoro-17-phenyl-18,19,20-trinor-;
2a,2b-dihomo-16,16-difluoro-17-phenyl-18,19,20-trinor-;
2a,2b-dihomo-15-methyl-16,16-difluoro-17-phenyl-18,19,20-trinor-;
2a,2b-dihomo-16-phenoxy-17,18,19,20-tetranor-;
2a,2b-dihomo-16-(m-trifluoromethylphenoxy)-17,18,19,20-tetranor-;
2a,2b-dihomo-16-(m-chlorophenoxy)-17,18,19,20-tetranor-;
2a,2b-dihomo-16-(p-fluorophenoxy)-17,18,19,20-tetranor-;
2a,2b-dihomo-15-methyl-16-phenoxy-17,18,19,20-tetranor-;
2a,2b-dihomo-16-phenoxy-18,19,20-trinor-;
2a,2b-dihomo-15-methyl-16-phenoxy-18,19,20-trinor-;
2a,2b-dihomo-16-methyl-16-phenoxy-18,19,20-trinor-;
2a,2b-dihomo-16-methyl-13,14-didehydro-;
2a,2b-dihomo-16,16-dimethyl-13,14-didehydro-;
2a,2b-dihomo-16-fluoro-13,14-didehydro-;
2a,2b-dihomo-16,16-difluoro-13,14-didehydro-;
2a,2b-dihomo-15-methyl-16,16-difluoro-13,14-didehydro-;
2a,2b-dihomo-17-phenyl-18,19,20-trinor-13,14-didehydro-;
2a,2b-dihomo-17-(m-trifluoromethylphenyl)-18,19,20-trinor-13,14-didehydro-;
2a,2b-dihomo-17-(m-chlorophenyl)-18,19,20-trinor-13,14-didehydro-;
2a,2b-dihomo-17-(p-fluorophenyl)-18,19,20-trinor-13,14-didehydro-;
2a,2b-dihomo-15-methyl-17-phenyl-18,19,20-trinor-13,14-didehydro-;
2a,2b-dihomo-16-methyl-17-phenyl-18,19,20-trinor-13,14-didehydro-;
2a,2b-dihomo-16,16-dimethyl-17-phenyl-18,19,20-trinor-13,14-didehydro-;
2a,2b-dihomo-16-fluoro-17-phenyl-18,19,20-trinor-13,14-didehydro-;
2a,2b-dihomo-16,16-difluoro-17-phenyl-18,19,20-trinor-13,14-dihydro-;
2a,2b-dihomo-16-phenoxy-17,18,19,20-tetranor-13,14-didehydro-;
2a,2b-dihomo-16-(m-trifluoromethylphenoxy)-17,18,19,20-tetranor-13,14-didehydro-;
2a,2b-dihomo-16-(m-chlorophenoxy)-17,18,19,20-tetranor-13,14-didehydro-;
2a,2b-dihomo-15-methyl-16-phenoxy-17,18,19,20-tetranor-;
13,14-didehydro-;
2a,2b-dihomo-16-phenoxy-18,19,20-trinor-13,14-didehydro-;
2a,2b-dihomo-16-methyl-16-phenoxy-18,19,20-trinor-13,14-didehydro-;

2a,2b-dihomo-13,14-dihydro-;
2a,2b-dihomo-15-methyl-13,14-dihydro-;
2a,2b-dihomo-16-methyl-13,14-dihydro-;
2a,2b-dihomo-16,16-dimethyl-13,14-dihydro-;
2a,2b-dihomo-16-fluoro-13,14-dihydro-;
2a,2b-dihomo-16,16-difluoro-13,14-dihydro-;
16-methyl-2a,2b-dihomo-16,16-tetrafluoro-13,14-dihydro-;
2a,2b-dihomo-17-phenyl-18,19,20-trinor-13,14-dihydro-;
2a,2b-dihomo-17-(m-trifluoromethylphenyl)-18,19,20-trinor-13,14-dihydro-;
2a,2b-dihomo-17-(m-chlorophenyl)-18,19,20-trinor-13,14-dihydro-;
2a,2b-dihomo-17-(p-fluorophenyl)-18,19,20-trinor-13,14-dihydro-;
2a,2b-dihomo-15-methyl-17-phenyl-18,19,20-trinor-13,14-dihydro-;
2a,2b-dihomo-16-methyl-17-phenyl-18,19,20-trinor-13,14-dihydro-;
2a,2b-dihomo-16,16-dimethyl-17-phenyl-18,19,20-trinor-13,14-dihydro-;
2a,2b-dihomo-16-fluoro-17-phenyl-18,19,20-dihydro-;
2a,2b-dihomo-16,16-difluoro-17-phenyl-18,19,20-dihydro-;
2a,2b-dihomo-16-phenoxy-17,18,19,20-tetranor-13,14-dihydro-;
2a,2b-dihomo-16-(m-trifluoromethylphenoxy)-17,18,19,20-tetranor-13,14-dihydro-;
2a,2b-dihomo-16-(m-chlorophenoxy)-17,18,19,20-tetranor-13,14-dihydro-;
2a,2b-dihomo-16-(p-fluorophenoxy)-17,18,19,20-tetranor-13,14-dihydro-;
2a,2b-dihomo-15-methyl-16-phenoxy-17,18,19,20-tetranor-13,14-dihydro-;
2a,2b-dihomo-16-phenoxy-18,19,20-trinor-13,14-dihydro-;
2a,2b-dihomo-15-methyl-16-phenoxy-18,19,20-trinor-13,14-dihydro-;
2a,2b-dihomo-16-methyl-16-phenoxy-18,19,20-trinor-13,14-dihydro-;
2a,2b-dihomo-cis-13-;
2a,2b-dihomo-15-methyl-cis-13-;
2a,2b-dihomo-16-methyl-cis-13-;
2a,2b-dihomo-16,16-dimethyl-cis-13-;
2a,2b-dihomo-16-fluoro-cis-13-;
2a,2b-dihomo-16,16-difluoro-cis-13-;
2a,2b-dihomo-15-methyl-16,16-difluoro-cis-13-;
2a,2b-dihomo-17-phenyl-18,19,20-trinor-cis-13-;
2a,2b-dihomo-17-(m-trifluoromethylphenyl)-18,19,20-trinor-cis-13-;
2a,2b-dihomo-17-(m-chlorophenyl)-18,19,20-trinor-cis-13-;
2a,2b-dihomo-17-(p-fluorophenyl)-18,19,20-trinor-cis-13-;
2a,2b-dihomo-15-methyl-17-phenyl-18,19,20-trinor-cis-13-;
2a,2b-dihomo-16-methyl-17-phenyl-18,19,20-trinor-cis-13-;
2a,2b-dihomo-16,16-dimethyl-17-phenyl-18,19,20-trinor-cis-13-;
2a,2b-dihomo-16-fluoro-17-phenyl-18,19,20-trinor-cis-13-;
2a,2b-dihomo-16,16-difluoro-17-phenyl-18,19,20-trinor-cis-13-;
2a,2b-dihomo-15-methyl-16,16-difluoro-17-phenyl-18,19,20-trinor-cis-13-;
2a,2b-dihomo-16-phenoxy-17,18,19,20-tetranor-cis-13-;
2a,2b-dihomo-16-(m-trifluoromethyl)-17,18,19,20-tetranor-cis-13-;
2a,2b-dihomo-16-(m-chlorophenoxy)-17,18,19,20-tetranor-cis-13-;
2a,2b-dihomo-16-(p-fluorophenoxy)-17,18,19,20-tetranor-cis-13-;
2a,2b-dihomo-15-methyl-16-phenoxy-17,18,19,20-tetranor-cis-13-;
2a,2b-dihomo-16-phenoxy-18,19,20-trinor-cis-13-;
2a,2b-dihomo-15-methyl-16-phenoxy-18,19,20-trinor-cis-13-;
2a,2b-dihomo-16-methyl-16-phenoxy-18,19,20-trinor-cis-13-;

Following the procedure of the above examples, but employing the appropriate starting material as described above, there are prepared
11a-Methano-TXA$_1$-type compounds;
11a-Methano-15,16-didehydro-15-deoxy-TXA$_1$-type compounds; or
11a-Methano-15-deoxy-TXA$_1$-type compounds in free acid, ester, or amide form, or as corresponding 2-decarboxy-2-aminomethyl or 2-decarboxy-2-hydroxymethyl derivatives which exhibit the following side chain variations:
15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;

16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
15-methyl-16,16-difluoro-17-phenyl-18,19,20-trinor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
cis-13-;
15-methyl-cis-13-;
16-methyl-cis-13-;
16,16-dimethyl-cis-13-;
16-fluoro-cis-13-;
16,16-difluoro-cis-13-;
15-methyl-16,16-difluoro-cis-13-;
17-phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
15-17-phenyl-18,19,20-trinor-cis-13-;
16-methyl-17-phenyl-18,19,20-trinor-cis-13-;
16,16-dimethyl-17-phenyl-18,19,20-trinor-cis-13-;
16-fluoro-17-phenyl-18,19,20-trinor-cis-13-;
16,16-difluoro-17-phenyl-18,19,20-trinor-cis-13-;
15-methyl-16,16-difluoro-17-phenyl-18,19,20-trinor-cis-13-;
16-phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
15-methyl-16-phenoxy-17,18,19,20-tetranor-cis-13-;
16-phenoxy-18,19,20-trinor-cis-13-;
15-methyl-16-phenoxy-18,19,20-trinor-cis-13-;
16-methyl-16-phenoxy-18,19,20-trinor-cis-13-;
3,7-inter-m-phenylene-4,5,6-trinor-;
3,7-inter-m-phenylene-4,5,6-trinor-15-methyl-;
3,7-inter-m-phenylene-4,5,6-trinor-16-methyl-;
3,7-inter-m-phenylene-4,5,6-trinor-16,16-dimethyl-;
3,7-inter-m-phenylene-4,5,6-trinor-16-fluoro-;
3,7-inter-m-phenylene-4,5,6-trinor-16,16-difluoro-;
3,7-inter-m-phenylene-4,5,6-trinor-15-methyl-16,16-difluoro-;
3,7-inter-m-phenylene-4,5,6-trinor-17-phenyl-18,19,20-trinor-;
3,7-inter-m-phenylene-4,5,6-trinor-17-(m-trifluoromethylphenyl)-18,19,20-trinor-;
3,7-inter-m-phenylene-4,5,6-trinor-17-(m-chlorophenyl)-18,19,20-trinor-;
3,7-inter-m-phenylene-4,5,6-trinor-17-(p-fluorophenyl)-18,19,20-trinor-;
3,7-inter-m-phenylene-4,5,6-trinor-15-methyl-17-phenyl-18,19,20-trinor-;
3,7-inter-m-phenylene-4,5,6-trinor-16-methyl-17-phenyl-18,19,20-trinor-;
3,7-inter-m-phenylene-4,5,6-trinor-16,16-dimethyl-17-phenyl-18,19,20-trinor-;
3,7-inter-m-phenylene-4,5,6-trinor-16-fluoro-17-phenyl-18,19,20-trinor-;
3,7-inter-m-phenylene-4,5,6-trinor-16,16-difluoro-17-phenyl-18,19,20-trinor-;
3,7-inter-m-phenylene-4,5,6-trinor-16-phenoxy-17,18,19,20-tetranor-;
3,7-inter-m-phenylene-4,5,6-trinor-16-(m-trifluoromethyl phenoxy)-17,18,19,20-tetranor-;
3,7-inter-m-phenylene-4,5,6-trinor-16-(m-chlorophenoxy)-17,18,19,20-tetranor-;
3,7-inter-m-phenylene-4,5,6-trinor-16-(p-fluorophenoxy)-17,18,19,20-tetranor-;
3,7-inter-m-phenylene-4,5,6-trinor-15-methyl-16-phenoxy-17,18,19,20-tetranor-;
3,7-inter-m-phenylene-4,5,6-trinor-16-phenoxy-18,19,20-trinor-;
3,7-inter-m-phenylene-4,5,6-trinor-15-methyl-16-phenoxy-18,19,20-trinor-;
3,7-inter-m-phenylene-4,5,6-trinor-13,14-didehydro-;
3,7-inter-m-phenylene-4,5,6-trinor-15-methyl-13,14-didehydro-;
3,7-inter-m-phenylene-4,5,6-trinor-16-methyl-13,14-didehydro-;
3,7-inter-m-phenylene-4,5,6-trinor-16,16-dimethyl-13,14-didehydro-;
3,7-inter-m-phenylene-4,5,6-trinor-16-fluoro-13,14-didehydro-;
3,7-inter-m-phenylene-4,5,6-trinor-16,16-difluoro-13,14-didehydro-;
3,7-inter-m-phenylene-4,5,6-trinor-17-phenyl-18,19,20-trinor-13,14-didehydro-;
3,7-inter-m-phenylene-4,5,6-trinor-17-(m-trifluoromethylphenyl-18,19,20-trinor-13,14-didehydro-;
3,7-inter-m-phenylene-4,5,6-trinor-17-(m-chlorophenyl)-18,19,20-trinor-13,14-didehydro-;
3,7-inter-m-phenylene-14,5,6-trinor-17-(p-fluorophenyl)-18,19,20-trinor-13,14-didehydro-;
3,7-inter-m-phenylene-4,5,6-trinor-15-methyl-17-phenyl-18,19,20-trinor-13,14-didehydro-;
3,7-inter-m-phenylene-4,5,6-trinor-16-methyl-17-phenyl-18,19,20-trinor-13,14-didehydro-;
3,7-inter-m-phenylene-4,5,6-trinor-16,16-dimethyl-17-phenyl-18,19,20-trinor-13,14-didehydor-;
3,7-inter-m-phenylene-4,5,6-trinor-16-fluoro-17-phenyl-18,19,20-trinor-13,14-didehydro-;

3,7-inter-m-phenylene-4,5,6-trinor-16,16-difluoro-17-phenyl-18,19,20-trinor-13,14-didehydro-;
3,7-inter-m-phenylene-4,5,6-trinor-16-phenoxy-17,18,19,20-tetranor-13,14-didehydro-;
3,7-inter-m-phenylene-4,5,6-trinor-16-(m-trifluoromethyl phenoxy)-17,18,19,20-tetranor-13,14-didehydro-;
3,7-inter-m-phenylene-4,5,6-trinor-16-(m-chlorophenoxy)-17,18,19,20-tetranor-13,14-didehydro-;
3,7-inter-m-phenylene-4,5,6-trinor-15-methyl-16-phenoxy-17,18,19,20-tetranor-13,14-didehydro-;
3,7-inter-m-phenylene-4,5,6-trinor-16-phenoxy-18,19,20-trinor-13,14-didehydro-;
3,7-inter-m-phenylene-4,5,6-trinor-15-methyl-16-phenoxy-18,19,20-trinor-13,14-didehydro-;
3,7-inter-m-phenylene-4,5,6-trinor-16-methyl-16-phenoxy-18,19,20-trinor-13,14-didehydro-;
3,7-inter-m-phenylene-4,5,6-trinor-15-methyl-13,14-dihydro-;
3,7-inter-m-phenylene-4,5,6-trinor-16-methyl-13,14-dihydro-;
3,7-inter-m-phenylene-4,5,6-trinor-16,16-dimethyl-13,14-dihydro-;
3,7-inter-m-phenylene-4,5,6-trinor-16-fluoro-13,14-dihydro-;
3,7-inter-m-phenylene-4,5,6-trinor-16,16-difluoro-13,14-dihydro-;
3,7-inter-m-phenylene-4,5,6-trinor-15-methyl-16,16-difluoro-13,14-dihydro-;
3,7-inter-m-phenylene-4,5,6-trinor-17-phenyl-18,19,20-trinor-13,14-dihydro-;
3,7-inter-m-phenylene-4,5,6-trinor-17-(m-trifluoromethyl phenyl)-18,19,20-trinor-13,14-dihydro-;
3,7-inter-m-phenylene-4,5,6-trinor-17-(m-chlorophenyl)-18,19,20-trinor-13,14-dihydro-;
3,7-inter-m-phenylene-4,5,6-trinor-17-(p-fluorophenyl)-18,19,20-trinor-13,14-dihydro-;
3,7-inter-m-phenylene-4,5,6-trinor-15-methyl-17-phenyl-18,19,20-trinor-13,14-dihydro-;
3,7-inter-m-phenylene-4,5,6-trinor-16-methyl-17-phenyl-18,19,20-trinor-13,14-dihydro-;
3,7-inter-m-phenylene-4,5,6-trinor-16,16-dimethyl-17-phenyl-18,19,20-trinor-13,14-dihydro-;
3,7-inter-m-phenylene-4,5,6-trinor-16-fluoro-17-phenyl-18,19,20-trinor-13,14-dihydro-;
3,7-inter-m-phenylene-4,5,6-trinor-16,16-difluoro-17-phenyl-18,19,20-trinor-13,14-dihydro-;
3,7-inter-m-phenylene-4,5,6-trinor-16-phenoxy-17,18,19,20-tetranor-13,14-dihydro-;
3,7-inter-m-phenylene-4,5,6-trinor-15-methyl-16-phenoxy-17,18,19,20-tetranor-13,14-dihydro-;
3,7-inter-m-phenylene-4,5,6-trinor-16-(m-trifluoromethyl-phenoxy)-17,18,19,20-tetranor-13,14-dihydro-;
3,7-inter-m-phenylene-4,5,6-trinor-16-(m-chlorohenoxy)-17,18,19,20-tetranor-13,14-dihydro-;
3,7-inter-m-phenylene-4,5,6-trinor-16-(p-fluorophenoxy)-17,18,19,20-tetranor-13,14-dihydro-;
3,7-inter-m-phenylene-4,5,6-trinor-15-methyl-16,16-difluoro-17-phenyl-18,19,20-trinor-13,14-dihydro-;
3,7-inter-m-phenylene-4,5,6-trinor-16-phenoxy-18,19,20-trinor-13,14-dihydro-;
3,7-inter-m-phenylene-4,5,6-trinor-15-methyl-16-phenoxy-18,19,20-trinor-13,14-dihydro-;
3,7-inter-m-phenylene-4,5,6-trinor-16-methyl-16-phenoxy-18,19,20-trinor-13,14-dihydro-;
3,7-inter-m-phenylene-4,5,6-trinor-cis-13-;
3,7-inter-m-phenylene-4,5,6-trinor-15-methyl-cis-13-;
3,7-inter-m-phenylene-4,5,6-trinor-16-methyl-cis-13-;
3,7-inter-m-phenylene-4,5,6-trinor-16,16-dimethyl-cis-13-;
3,7-inter-m-phenylene-4,5,6-trinor-16-fluoro-cis-13-;
3,7-inter-m-phenylene-4,5,6-trinor-16,16-difluoro-cis-13-;
3,7-inter-m-phenylene-4,5,6-trinor-15-methyl-16,16-difluoro-cis-13-;
3,7-inter-m-phenylene-4,5,6-trinor-17-phenyl-18,19,20-trinor-cis-13-;
3,7-inter-m-phenylene-4,5,6-trinor-17-(m-trifluoromethyl phenyl)-18,19,20-trinor-cis-13-;
3,7-inter-m-phenylene-4,5,6-trinor-17-(m-chlorophenyl)-18,19,20-trinor-cis-13-;
3,7-inter-m-phenylene-4,5,6-trinor-17-(p-fluorophenyl)-18,19,20-trinor-cis-13-;
3,7-inter-m-phenylene-4,5,6-trinor-15-methyl-17-phenyl-18,19,20-trinor-cis-13-;
3,7-inter-m-phenylene-4,5,6-trinor-16-methyl-17-phenyl-18,19,20-trinor-cis-13-;
3,7-inter-m-phenylene-4,5,6-trinor-16,16-dimethyl-17-phenyl-18,19,20-trinor-cis-13-;
3,7-inter-m-phenylene-4,5,6-trinor-16-fluoro-17-phenyl-18,19,20-trinor-cis-13-;
3,7-inter-m-phenylene-4,5,6-trinor-16,16-difluoro-17-phenyl-18,19,20-trinor-cis-13-;
3,7-inter-m-phenylene-4,5,6-trinor-15-methyl-16,16-difluoro-17-phenyl-18,19,20-trinor-cis-13-;
3,7-inter-m-phenylene-4,5,6-trinor-16-phenoxy-17,18,19,20-tetranor-cis-13-;
3,7-inter-m-phenylene-4,5,6-trinor-16-(m-trifluoromethyl phenoxy)-17,18,19,20-tetranor-cis-13-;
3,7-inter-m-phenylene-4,5,6-trinor-16-(m-chlorophenoxy)-17,18,19,20-tetranor-cis-13-;
3,7-inter-m-phenylene-4,5,6-trinor-16-(p-fluorophenoxy)-17,18,19,20-tetranor-cis-13-;
3,7-inter-m-phenylene-4,5,6-trinor-15-methyl-16-phenoxy-17,18,19,20-tetranor-cis-13-;
3,7-inter-m-phenylene-4,5,6-trinor-16-phenoxy-18,19,20-trinor-cis-13-;
3,7-inter-m-phenylene-4,5,6-trinor-15-methyl-16-phenoxy-18,19,20-trinor-cis-13-;
3,7-inter-m-phenylene-16-methyl-16-phenoxy-18,19,20-trinor-cis-13-;
3,7-inter-m-phenylene-4,5,6-trinor-3-oxa-;
3,7-inter-m-phenylene-4,5,6-trinor-3-oxa-15-methyl-;
3,7-inter-m-phenylene-4,5,6-trinor-3-oxa-16-methyl-;
3,7-inter-m-phenylene-4,5,6-trinor-3-oxa-16,16-dimethyl-;
3,7-inter-m-phenylene-4,5,6-trinor-3-oxa-16-fluoro-;
3,7-inter-m-phenylene-4,5,6-trinor-3-oxa-16,16-difluoro-;
3,7-inter-m-phenylene-4,5,6-trinor-3-oxa-15-methyl-16,16-difluoro-;
3,7-inter-m-phenylene-4,5,6-trinor-3-oxa-17-phenyl-18,19,20-trinor-;
3,7-inter-m-phenylene-4,5,6-trinor-3-oxa-17-(m-trifluoromethylphenyl)-18,19,20-trinor-;
3,7-inter-m-phenylene-4,5,6-trinor-3-oxa-17-(m-chlorophenyl)-18,19,20-trinor-;
3,7-inter-m-phenylene-4,5,6-trinor-3-oxa-17-(p-fluoro phenyl)-18,19,20-trinor-;
3,7-inter-m-phenylene-4,5,6-trinor-3-oxa-15-methyl-17-phenyl-18,19,20-trinor-;
3,7-inter-m-phenylene-4,5,6-trinor-3-oxa-16-methyl-17-phenyl-18,19,20-trinor-;
3,7-inter-m-phenylene-4,5,6-trinor-3-oxa-16,16-dimethyl-17-phenyl-18,19,20-trinor-;

3,7-inter-m-phenylene-4,5,6-trinor-3-oxa-16-fluoro-17-phenyl-18,19,20-trinor-;
3,7-inter-m-phenylene-4,5,6-trinor-3-oxa-16,16-difluoro-17-phenyl-18,19,20-trinor-;
3,7-inter-m-phenylene-4,5,6-trinor-3-oxa-16-phenoxy-17,18,19,20-tetranor-;
3,7-inter-m-phenylene-4,5,6-trinor-3-oxa-16-(m-trifluoro methylphenoxy)-17,18,19,20-tetranor-;
3,7-inter-m-phenylene-4,5,6-trinor-3-oxa-16-(m-chloro phenoxy)-17,18,19,20-tetranor-;
3,7-inter-m-phenylene-4,5,6-trinor-3-oxa-16-(p-fluoro phenoxy)-17,18,19,20-tetranor-;
3,7-inter-m-phenylene-4,5,6-trinor-3-oxa-15-methyl-16-phenoxy-17,18,19,20-tetranor-;
3,7-inter-m-phenylene-4,5,6-trinor-3-oxa-16-phenoxy-18,19,20-trinor-;
3,7-inter-m-phenylene-4,5,6-trinor-3-oxa-15-methyl-16-phenoxy-18,19,20-trinor-;
3,7-inter-m-phenylene-4,5,6-trinor-3-oxa-13,14-didehydro-;
3,7-inter-m-phenylene-4,5,6-trinor-3-oxa-15-methyl-13,14-didehydro-;
3,7-inter-m-phenylene-4,5,6-trinor-3-oxa-16-methyl-13,14-didehydro-;
3,7-inter-m-phenylene-4,5,6-trinor-3-oxa-16,16-dimethyl-13,14-didehydro-;
3,7-inter-m-phenylene-4,5,6-trinor-3-oxa-16-fluoro-13,14-didehydro-;
3,7-inter-m-phenylene-4,5,6-trinor-3-oxa-16,16-difluoro-13,14-didehydro-;
3,7-inter-m-phenylene-4,5,6-trinor-3-oxa-17-phenyl-18,19,20-trinor-13,14-didehydro-;
3,7-inter-m-phenylene-4,5,6-trinor-3-oxa-17-(m-trifluoromethylphenyl)-18,19,20-trinor-13,14-didehydro-;
3,7-inter-m-phenylene-4,5,6-trinor-3-oxa-17-(m-chlorophenyl)-18,19,20-trinor-13,14-didehydro-;
3,7-inter-m-phenylene-4,5,6-trinor-3-oxa-17-(p-fluorophenyl)-18,19,20-trinor-13,14-didehydro-;
3,7-inter-m-phenylene-4,5,6-trinor-3-oxa-15-methyl-17-phenyl-18,19,20-trinor-13,14-didehydro-;
3,7-inter-m-phenylene-4,5,6-trinor-3-oxa-16-methyl-17-phenyl-18,19,20-trinor-13,14-didehydro-;
3,7-inter-m-phenylene-4,5,6-trinor-3-oxa-16,16-dimethyl-17-phenyl-18,19,20-trinor-13,14-didehydro-;
3,7-inter-m-phenylene-4,5,6-trinor-3-oxa-16-fluoro-17-phenyl-18,19,20-trinor-13,14-didehydro-;
3,7-inter-m-phenylene-4,5,6-trinor-3-oxa-16,16-difluoro-17-phenyl-18,19,20-trinor-13,14-didehydro-;
3,7-inter-m-phenylene-4,5,6-trinor-3-oxa-16-phenoxy-17,18,19,20-tetranor-13,14-didehydro-;
3,7-inter-m-phenylene-4,5,6-trinor-3-oxa-16-(m-trifluoromethylphenoxy)-17,18,19,20-tetranor-13,14-didehydro-;
3,7-inter-m-phenylene-4,5,6-trinor-3-oxa-16-(m-chlorophenoxy)-17,18,19,20-tetranor-13,14-didehydro-;
3,7-inter-m-phenylene-4,5,6-trinor-3-oxa-15-methyl-16-phenoxy-17,18,19,20-tetranor-13,14-didehydro-;
3,7-inter-m-phenylene-4,5,6-trinor-3-oxa-16-phenoxy-18,19,20-trinor-13,14-didehydro-;
3,7-inter-m-phenylene-4,5,6-trinor-3-oxa-15-methyl-16-phenoxy-18,19,20-trinor-13,14-didehydro-;
3,7-inter-m-phenylene-4,5,6-trinor-3-oxa-16-methyl-16-phenoxy-18,19,20-trinor-13,14-didehydro-;
3,7-inter-m-phenylene-4,5,6-trinor-3-oxa-15-methyl-13,14-dihydro-;
3,7-inter-m-phenylene-4,5,6-trinor-3-oxa-16-methyl-13,14-dihydro-; 3,7-inter-m-phenylene-4,5,6-trinor-3-oxa-16,16-dimethyl-13,14-dihydro-;
3,7-inter-m-phenylene-4,5,6-trinor-3-oxa-16-fluoro-13,14-dihydro-;
3,7-inter-m-phenylene-4,5,6-trinor-3-oxa-16,16-difluoro-13,14-dihydro-;
3,7-inter-m-phenylene-4,5,6-trinor-3-oxa-15-methyl-16,16-difluoro-13,14-dihydro-;
3,7-inter-m-phenylene-4,5,6-trinor-3-oxa-17-phenyl-18,19,20-trinor-13,14-dihydro-;
3,7-inter-m-phenylene-4,5,6-trinor-3-oxa-17-(m-trifluoromethylphenyl)-18,19,20-trinor-13,14-dihydro-;
3,7-inter-m-phenylene-4,5,6-trinor-3-oxa-17-(m-chlorophenyl)-18,19,20-trinor-13,14-dihydro-;
3,7-inter-m-phenylene-4,5,6-trinor-3-oxa-17-(p-fluorophenyl)-18,19,20-trinor-13,14-dihydro-;
3,7-inter-m-phenylene-4,5,6-trinor-3-oxa-15-methyl-17-phenyl-18,19,20-trinor-13,14-dihydro-;
3,7-inter-m-phenylene-4,5,6-trinor-3-oxa-16-methyl-17-phenyl-18,19,20-trinor-13,14-dihydro-;
3,7-inter-m-phenylene-4,5,6-trinor-3-oxa-16,16-dimethyl-17-phenyl-18,19,20-trinor-13,14-dihydro-;
3,7-inter-m-phenylene-4,5,6-trinor-3-oxa-16-fluoro-17-phenyl-18,19,20-trinor-13,14-dihydro-;
3,7-inter-m-phenylene-4,5,6-trinor-3-oxa-16,16-difluoro-17-phenyl-18,19,20-trinor-13,14-dihydro-;
3,7-inter-m-phenylene-4,5,6-trinor-3-oxa-16-phenoxy-17,18,19,20-tetranor-13,14-dihydro-;
3,7-inter-m-phenylene-4,5,6-trinor-3-oxa-15-methyl-16-phenoxy-17,18,19,20-tetranor-13,14-dihydro-;
3,7-inter-m-phenylene-4,5,6-trinor-3-oxa-16-(m-trifluoromethylphenoxy)-17,18,19,20-tetranor-13,14-dihydro-;
3,7-inter-m-phenylene-4,5,6-trinor-3-oxa-16-(m-chlorophenoxy)-17,18,19,20-tetranor-13,14-dihydro-;
3,7-inter-m-phenylene-4,5,6-trinor-3-oxa-16-(p-fluorophenoxy)-17,18,19,20-tetranor-13,14-dihydro-;
3,7-inter-m-phenylene-4,5,6-trinor-3-oxa-15-methyl-16,16-difluoro-17-phenyl-18,19,20-trinor-13,14-dihydro-;
3,7-inter-m-phenylene-4,5,6-trinor-3-oxa-16-phenoxy-18,19,20-trinor-13,14-dihydro-;
3,7-inter-m-phenylene-4,5,6-trinor-3-oxa-15-methyl-16-phenoxy-18,19,20-trinor-13,14-dihydro-;
3,7-inter-m-phenylene-4,5,6-trinor-3-oxa-16-methyl-16-phenoxy-18,19,20-trinor-13,14-dihydro-;
3,7-inter-m-phenylene-4,5,6-trinor-3-oxa-cis-13-;
3,7-inter-m-phenylene-4,5,6-trinor-3-oxa-15-methyl-cis-13-;
3,7-inter-m-phenylene-4,5,6-trinor-3-oxa-16-methyl-cis-13-;
3,7-inter-m-phenylene-4,5,6-trinor-3-oxa-16,16-dimethyl-cis-13-;
3,7-inter-m-phenylene-4,5,6-trinor-3-oxa-16-fluoro-cis-13-;
3,7-inter-m-phenylene-4,5,6-trinor-3-oxa-16,16-difluoro-cis-13-;
3,7-inter-m-phenylene-4,5,6-trinor-3-oxa-15-methyl-16,16-difluoro-cis-13-;
3,7-inter-m-phenylene-4,5,6-trinor-3-oxa-17-phenyl-18,19,20-trinor-cis-13-;
3,7-inter-m-phenylene-4,5,6-trinor-3-oxa-17-(m-trifluoromethylphenyl)-18,19,20-trinor-cis-13-;
3,7-inter-m-phenylene-4,5,6-trinor-3-oxa-17-(m-chlorophenyl)-18,19,20-trinor-cis-13-;
3,7-inter-m-phenylene-4,5,6-trinor-3-oxa-17-(p-fluorophenyl)-18,19,20-trinor-cis-13-;

3,7-inter-m-phenylene-4,5,6-trinor-3-oxa-15-methyl-17-phenyl-18,19,20-trinor-cis-13-;
3,7-inter-m-phenylene-4,5,6-trinor-3-oxa-16-methyl-17-phenyl-18,19,20-trinor-cis-13-;
3,7-inter-m-phenylene-4,5,6-trinor-3-oxa-16,16-dimethyl-17-phenyl-18,19,20-trinor-cis-13-;
3,7-inter-m-phenylene-4,5,6-trinor-3-oxa-16-fluoro-17-phenyl-18,19,20-trinor-cis-13-;
3,7-inter-m-phenylene-4,5,6-trinor-3-oxa-16,16-difluoro-17-phenyl-18,19,20-trinor-cis-13-;
3,7-inter-m-phenylene-4,5,6-trinor-3-oxa-15-methyl-16,16-difluoro-17-phenyl-18,19,20-trinor-cis-13-;
3,7-inter-m-phenylene-4,5,6-trinor-3-oxa-16-phenoxy-17,18,19,20-tetranor-cis-13-;
3,7-inter-m-phenylene-4,5,6-trinor-3-oxa-16-(m-trifluoromethylphenoxy)-17,18,19,20-tetranor-cis-13-;
3,7-inter-m-phenylene-4,5,6-trinor-3-oxa-16-(m-chlorophenoxy)-17,18,19,20-tetranor-cis-13-;
3,7-inter-m-phenylene-4,5,6-trinor-3-oxa-16-(p-fluorophenoxy)-17,18,19,20-tetranor-cis-13-;
3,7-inter-m-phenylene-4,5,6-trinor-3-oxa-15-methyl-16-phenoxy-17,18,19,20-tetranor-cis-13-;
3,7-inter-m-phenylene-4,5,6-trinor-3-oxa-16-phenoxy-18,19,20-trinor-cis-13-;
3,7-inter-m-phenylene-4,5,6-trinor-3-oxa-15-methyl-16-phenoxy-18,19,20-trinor-cis-13-;
3,7-inter-m-phenylene-4,5,6-trinor-3-oxa-16-methyl-16-phenoxy-18,19,20-trinor-cis-13-;
2,2-difluoro-;
2,2-difluoro-15-methyl-;
2,2-difluoro-16-methyl-;
2,2-difluoro-16,16-dimethyl-;
2,2,16-trifluoro-;
2,2,16,16-tetrafluoro-;
2,2,16,16-tetrafluoro-15-methyl-;
2,2-difluoro-17-phenyl-18,19,20-trinor-;
2,2-difluoro-15-methyl-17-phenyl-18,19,20-trinor-;
2,2-difluoro-17-(m-trifluoromethylphenyl)-18,19,20-trinor-;
2,2-difluoro-17-(m-chlorophenyl)-18,19,20-trinor-;
2,2-difluoro-17-(p-fluorophenyl)-18,19,20-trinor-;
2,2-difluoro-16-methyl-17-phenyl-18,19,20-trinor-;
2,2-difluoro-16,16-dimethyl-17-phenyl-18,19,20-trinor-;
2,2,16-trifluoro-17-phenyl-18,19,20-trinor-;
2,2,16,16-tetrafluoro-17-phenyl-18,19,20-trinor-;
2,2,16,16-tetrafluoro-15-methyl-17-phenyl-18,19,20-trinor-;
2,2-difluoro-16-phenoxy-17,18,19,20-tetranor-;
2,2-difluoro-16-(m-trifluoromethylphenoxy)-17,18,19,20-tetranor-;
2,2-difluoro-16-(m-chlorophenoxy)-17,18,19,20-tetranor-;
2,2-difluoro-16-(p-fluorophenoxy)-17,18,19,20-tetranor-;
2,2-difluoro-15-methyl-16-phenoxy-17,18,19,20-tetranor-;
2,2-difluoro-16-phenoxy-18,19,20-trinor-;
2,2-difluoro-15-methyl-16-phenoxy-18,19,20-trinor-;
2,2-difluoro-16-methyl-16-phenoxy-18,19,20-trinor-;
2,2-difluoro-16-methyl-13,14-didehydro-;
2,2-difluoro-16,16-dimethyl-13,14-didehydro-;
2,2,16-trifluoro-13,14-didehydro-;
2,2,16,16-tetrafluoro-13,14-didehydro-;
2,2,16,16-tetrafluoro-15-methyl-13,14-didehydro-;
2,2-difluoro-17-phenyl-18,19,20-trinor-13,14-didehydro-;
2,2-difluoro-17-(m-trifluoromethylphenyl)-18,19,20-trinor-13,14-didehydro-;
2,2-difluoro-17-(m-chlorophenyl)-18,19,20-trinor-13,14-didehydro-;
2,2-difluoro-17-(p-fluorophenyl)-18,19,20-trinor-13,14-didehydro-;
2,2-fluoro-15-methyl-17-phenyl-18,19,20-trinor-13,14-didehydro-;
2,2-difluoro-16-methyl-17-phenyl-18,19,20-trinor-13,14-didehydro-;
2,2-difluoro-16,16-dimethyl-17-phenyl-18,19,20-trinor-13,14-didehydro-;
2,2,16-trifluoro-17-phenyl-18,19,20-trinor-13,14-didehydro-;
2,2,16,16-tetrafluoro-17-phenyl-18,19,20-trinor-13,14-didehydro-;
2,2-difluoro-16-phenoxy-17,18,19,20-tetranor-13,14-didehydro-;
2,2-difluoro-16-(m-trifluoromethylphenoxy)-17,18,19,20-tetranor-13,14-didehydro-;
2,2-difluoro-16-(m-chlorophenoxy)-17,18,19,20-tetranor-13,14-didehydro-;
2,2-difluoro-15-methyl-16-phenoxy-17,18,19,20-tetranor-; 13,14-didehydro-;
2,2-difluoro-16-phenoxy-18,19,20-trinor-13,14-didehydro-;
2,2-difluoro-16-methyl-16-phenoxy-18,19,20-trinor-13,14-didehydro-;
2,2-difluoro-13,14-dihydro-;
2,2-difluoro-15-methyl-13,14-dihydro-;
2,2-difluoro-16-methyl-13,14-dihydro-;
2,2-difluoro-16,16-dimethyl-13,14-dihydro-;
2,2,16-trifluoro-13,14-dihydro-;
2,2,16,16-tetrafluoro-13,14-dihydro-;
16-methyl-2,2,16,16-tetrafluoro-13,14-dihydro-;
2,2-difluoro-17-phenyl-18,19,20-trinor-13,14-dihydro-;
2,2-difluoro-17-(m-trifluoromethylphenyl)-18,19,20-trinor-13,14-dihydro-;
2,2-difluoro-17-(m-chlorophenyl)-18,19,20-trinor-13,14-dihydro-;
2,2-difluoro-17-(p-fluorophenyl)-18,19,20-trinor-13,14-dihydro-;
2,2-difluoro-15-methyl-17-phenyl-18,19,20-trinor-13,14-dihydro-;
2,2-difluoro-15-methyl-17-(p-fluorophenyl)-18,19,20-trinor-13,14-dihydro-;
2,2-difluoro-16-methyl-17-phenyl-18,19,20-trinor-13,14-dihydro-;
2,2-difluoro-16,16-dimethyl-17-phenyl-18,19,20-trinor-13,14-dihydro-;
2,2,16-trifluoro-17-phenyl-18,19,20-dihydro-;
2,2,16,16-tetrafluoro-17-phenyl-18,19,20-dihydro-;
2,2-difluoro-16-phenoxy-17,18,19,20-tetranor-13,14-dihydro-;
2,2-difluoro-16-(m-trifluoromethylphenoxy)-17,18,19,20-tetranor-13,14-dihydro-;
2,2-difluoro-16-(m-chlorophenoxy)-17,18,19,20-tetranor-13,14-dihydro-;
2,2-difluoro-16-(p-fluorophenoxy)-17,18,19,20-tetranor-13,14-dihydro-;
2,2-difluoro-15-methyl-16-phenoxy-17,18,19,20-tetranor-13,14-dihydro-;
2,2-difluoro-16-phenoxy-18,19,20-trinor-13,14-dihydro-;
2,2-difluoro-15-methyl-16-phenoxy-18,19,20-trinor-13,14-dihydro-;
2,2-difluoro-16-methyl-16-phenoxy-18,19,20-trinor-13,14-dihydro-;
2,2-difluoro-cis-13-;
15-methyl-2,2-difluoro-cis-13-;

2,2-difluoro-16-methyl-cis-13-;
2,2-difluoro-16,16-dimethyl-cis-13-;
2,2,16-trifluoro-cis-13-;
2,2,16,16-tetrafluoro-cis-13-;
2,2,16,16-tetrafluoro-15-methyl-cis-13-;
2,2-difluoro-17-phenyl-18,19,20-trinor-cis-13-;
2,2-difluoro-17-(m-trifluoromethylphenyl)-18,19,20-trinor-cis-13-;
2,2-difluoro-17-(m-chlorophenyl)-18,19,20-trinor-cis-13-;
2,2-difluoro-17-(p-fluorophenyl)-18,19,20-trinor-cis-13-;
2,2-difluoro-15-methyl-17-phenyl-18,19,20-trinor-cis-13-;
2,2-difluoro-16-methyl-17-phenyl-18,19,20-trinor-cis-13-;
2,2-difluoro-16,16-dimethyl-17-phenyl-18,19,20-trinor-cis-13-;
2,2,16-trifluoro-17-phenyl-18,19,20-trinor-cis-13-;
2,2,16,16-tetrafluoro-17-phenyl-18,19,20-trinor-cis-13-;
2,2,16,16-tetrafluoro-15-methyl-17-phenyl-18,19,20-trinor-cis-13-;
2,2-difluoro-16-phenoxy-17,18,19,20-tetranor-cis-13-;
2,2-difluoro-15-methyl-16-phenoxy-17,18,19,20-tetranor-cis-13-;
2,2-difluoro-16-(m-trifluoromethylphenoxy)-17,18,19,20-tetranor-cis-13-;
2,2-difluoro-16-(m-chlorophenoxy)-17,18,19,20-tetranor-cis-13-;
2,2-difluoro-16-(p-fluorophenoxy)-17,18,19,20-tetranor-cis-13-;
2,2-difluoro-16-phenoxy-18,19,20-trinor-cis-13-;
2,2-difluoro-15-methyl-16-phenoxy-18,19,20-trinor-cis-13-;
2,2-difluoro-16-methyl-16-phenoxy-18,19,20-trinor-cis-13-;
2a,2b-dihomo-;
2a,2b-dihomo-15-methyl-;
2a,2b-dihomo-16-methyl-;
2a,2b-dihomo-16,16-dimethyl-;
2a,2b-dihomo-16-fluoro-;
2a,2b-dihomo-16,16-difluoro-;
2a,2b-dihomo-15-methyl-16,16-difluoro-;
2a,2b-dihomo-17-phenyl-18,19,20-trinor-;
2a,2b-dihomo-17-(m-trifluoromethylphenyl)-18,19,20-trinor-;
2a,2b-dihomo-17-(m-chlorophenyl)-18,19,20-trinor-;
2a,2b-dihomo-17-(p-fluorophenyl)-18,19,20-trinor-;
2a,2b-dihomo-15-methyl-17-phenyl-18,19,20-trinor-;
2a,2-b-dihomo-16-methyl-17-phenyl-18,19,20-trinor-;
2a,2b-dihomo-16,16-dimethyl-17-phenyl-18,19,20-trinor-;
2a,2b-dihomo-16-fluoro-17-phenyl-18,19,20-trinor-;
2a,2b-dihomo-16,16-difluoro-17-phenyl-18,19,20-trinor-;
2a,2b-dihomo-15-methyl-16,16-difluoro-17-phenyl-18,19,20-trinor-;
2a,2b-dihomo-16-phenoxy-17,18,19,20-tetranor-;
2a,2b-dihomo-16-(m-trifluoromethylphenoxy)-17,18,19,20-tetranor-;
2a,2b-dihomo-16-(m-chlorophenoxy)-17,18,19,20-tetranor-;
2a,2b-dihomo-16-(p-fluorophenoxy)-17,18,19,20-tetranor-;
2a,2b-dihomo-15-methyl-16-phenoxy-17,18,19,20-tetranor-;
2a,2b-dihomo-16-phenoxy-18,19,20-trinor-;
2a,2b-dihomo-15-methyl-16-phenoxy-18,19,20-trinor-;
2a,2b-dihomo-16-methyl-16-phenoxy-18,19,20-trinor-;
2a,2b-dihomo-16-methyl-13,14-didehydro-;
2a,2b-dihomo-16,16-dimethyl-13,14-didehydro-;
2a,2b-dihomo-16-fluoro-13,14-didehydro-;
2a,2b-dihomo-16,16-difluoro-13,14-didehydro-;
2a,2b-dihomo-15-methyl-16,16-difluoro-13,14-didehydro-;
2a,2b-dihomo-17-phenyl-18,19,20-trinor-13,14-didehydro-;
2a,2b-dihomo-17-(m-trifluoromethylphenyl)-18,19,20-trinor-13,14-didehydro-;
2a,2b-dihomo-17-(m-chlorophenyl)-18,19,20-trinor-13,14-didehydro-;
2a,2b-dihomo-17-(p-fluorophenyl)-18,19,20-trinor-13,14-didehydro-;
2a,2b-dihomo-15-methyl-17-phenyl-18,19,20-trinor-13,14-didehydro-;
2a,2b-dihomo-16-methyl-17-phenyl-18,19,20-trinor-13,14-didehydro-;
2a,2b-dihomo-16,16-dimethyl-17-phenyl-18,19,20-trinor-13,14-didehydro-;
2a,2b-dihomo-16-fluoro-17-phenyl-18,19,20-trinor-13,14-didehydro-;
2a,2b-dihomo-16,16-difluoro-17-phenyl-18,19,20-trinor-13,14-dihydro-;
2a,2b-dihomo-16-phenoxy-17,18,19,20-tetranor-13,14-didehydro-;
2a,2b-dihomo-16-(m-trifluoromethylphenoxy)-17,18,19,20-tetranor-13,14-didehydro-;
2a,2b-dihomo-16-(m-chlorophenoxy)-17,18,19,20-tetranor-13,14-didehydro-;
2a,2b-dihomo-15-methyl-16-phenoxy-17,18,19,20-tetranor-; 13,14-didehydro-;
2a,2b-dihomo-16-phenoxy-18,19,20-trinor-13,14-didehydro-;
2a,2b-dihomo-16-methyl-16-phenoxy-18,19,20-trinor-13,14-didehydro-;
2a,2b-dihomo-13,14-dihydro-;
2a,2b-dihomo-15-methyl-13,14-dihydro-;
2a,2b-dihomo-16-methyl-13,14-dihydro-;
2a,2b-dihomo-16,16-dimethyl-13,14-dihydro-;
2a,2b-dihomo-16-fluoro-13,14-dihydro-;
2a,2b-dihomo-16,16-difluoro-13,14-dihydro-;
15-methyl-2a,2b-dihomo-16,16-difluoro-13,14-dihydro-;
2a,2b-dihomo-17-phenyl-18,19,20-trinor-13,14-dihydro-;
2a,2b-dihomo-17-(m-trifluoromethylphenyl)-18,19,20-trinor-13,14-dihydro-;
2a,2,b-dihomo-17-(m-chlorophenyl)-18,19,20-trinor-13,14-dihydro-;
2a,2b-dihomo-17-(p-fluorophenyl)-18,19,20-trinor-13,14-dihydro-;
2a,2b-dihomo-15-methyl-17-(p-fluorophenyl)-18,19,20-trinor-13,14-dihydro-;
2a,2b-dihomo-15-methyl-17-phenyl-18,19,20-trinor-13,14-dihydro-;
2a,2b-dihomo-16-methyl-17-phenyl-18,19,20-trinor-13,14-dihydro-;
2a,2b-dihomo-16,16-dimethyl-17-phenyl-18,19,20-trinor-13,14-dihydro-;
2a,2b-dihomo-16-fluoro-17-phenyl-18,19,20-dihydro-;
2a,2b-dihomo-16,16-difluoro-17-phenyl-18,19,20-dihydro-;
2a,2b-dihomo-16-phenoxy-17,18,19,20-tetranor-13,14-dihydro-;
2a,2b-dihomo-16-(m-trifluoromethylphenoxy)-17,18,19,20-tetranor-13,14-dihydro-;
2a,2b-dihomo-16-(m-chlorophenoxy)-17,18,19,20-tetranor-13,14-dihydro-;

2a,2b-dihomo-16-(p-fluorophenoxy)-17,18,19,20-tetranor-13,14-dihydro-;
2a,2b-dihomo-15-methyl-16-phenoxy-17,18,19,20-tetranor-13,14-dihydro-;
2a,2b-dihomo-16-phenoxy-18,19,20-trinor-13,14-dihydro-;
2a,2b-dihomo-15-methyl-16-phenoxy-18,19,20-trinor-13,14-dihydro-;
2a,2b-dihomo-16-methyl-16-phenoxy-18,19,20-trinor-13,14-dihydro-;
2a,2b-dihomo-cis-13-;
2a,2b-dihomo-15-methyl-cis-13-;
2a,2b-dihomo-16-methyl-cis-13-;
2a,2b-dihomo-16,16-dimethyl-cis-13-;
2a,2b-dihomo-16-fluoro-cis-13-;
2a,2b-dihomo-16,16-difluoro-cis-13-;
2a,2b-dihomo-15-methyl-16,16-difluoro-cis-13-;
2a,2b-dihomo-17-phenyl-18,19,20-trinor-cis-13-;
2a,2b-dihomo-17-(m-trifluoromethylphenyl)-18,19,20-trinor-cis-13-;
2a,2b-dihomo-17-(m-chlorophenyl)-18,19,20-trinor-cis-13-;
2a,2b-dihomo-17-(p-fluorophenyl)-18,19,20-trinor-cis-13-;
2a,2b-dihomo-15-methyl-17-phenyl-18,19,20-trinor-cis-13-;
2a,2b-dihomo-16-methyl-17-phenyl-18,19,20-trinor-cis-13-;
2a,2b-dihomo-16,16-dimethyl-17-phenyl-18,19,20-trinor-cis-13-;
2a,2b-dihomo-16-fluoro-17-phenyl-18,19,20-trinor-cis-13-;
2a,2b-dihomo-16,16-difluoro-17-phenyl-18,19,20-trinor-cis-13-;
2a,2b-dihomo-15-methyl-16,16-difluoro-17-phenyl-18,19,20-trinor-cis-13-;
2a,2b-dihomo-16-phenoxy-17,18,19,20-tetranor-cis-13-;
2a.2b-dihomo-16-(m-trifluoromethylphenoxy)-17,18,19,20-tetranor-cis-13-;
2a,2b-dihomo-16-(m-chlorophenoxy)-17,18,19,20-tetranor-cis-13-;
2a.2b-dihomo-16-(p-fluorophenoxy)-17,18,19,20-tetranor-cis-13-;
2a,2b-dihomo-15-methyl-16-phenoxy-17,18,19,20-tetranor-cis-13-;
2a,2b-dihomo-16-phenoxy-18,19,20-trinor-cis-13-;
2a,2b-dihomo-15-methyl-16-phenoxy-18,19,20-trinor-cis-13-;
2a,2b-dihomo-16-methyl-16-phenoxy-18,19,20-trinor-cis-13-;
cis-4,5-didehydro-;
cis-4,5-didehydro-15-methyl-;
cis-4,5-didehydro-15-methyl-17-(p-fluorophenyl)-18,19,20-trinor-13,14-dihydro-;
cis-4,5-didehydro-15-methyl-17-phenyl-18,19,20-trinor-13,14-dihydro-;
cis-4,5-didehydro-16-methyl-17-phenyl-18,19,20-trinor-13,14-dihydro-;
cis-4,5-didehydro-16,16-dimethyl-17-phenyl-18,19,20-trinor-13,14-dihydro-;
cis-4,5-didehydro-16-fluoro-17-phenyl-18,19,20-dihydro-;
cis-4,5-didehydro-16,16-difluoro-17-phenyl-18,19,20-trinor-dihydro-;
cis-4,5-didehydro-16-phenoxy-17,18,19,20-tetranor-13,14-dihydro-;
cis-4,5-didehydro-16-(m-trifluoromethylphenoxy)-17,18,19,20-tetranor-13,14-dihydro-;
cis-4,5-didehydro-16-(m-chlorophenoxy)-17,18,19,20-tetranor-13,14-dihydro-;
cis-4,5-didehydro-16-(p-fluorophenoxy)-17,18,19,20-tetranor-13,14-dihydro-;
cis-4,5-didehydro-15-methyl-16-phenoxy-17,18,19,20-tetranor-13,14-dihydro-;
cis-4,5-didehydro-16-phenoxy-18,19,20-trinor-13,14-dihydro-;
cis-4,5-didehydro-15-methyl-16-phenoxy-18,19,20-trinor-13,14-dihydro-;
cis-4,5-didehydro-16-methyl-16-phenoxy-18,19,20-trinor-13,14-dihydro-;
cis-4,5-didehydro-cis-13-;
cis-4,5-didehydro-15-methyl-cis-13-;
cis-4,5-didehydro-16-methyl-cis-13-;
cis-4,5-didehydro-16,16-dimethyl-cis-13-;
cis-4,5-didehydro-16-fluoro-cis-13-;
cis-4,5-didehydro-16,16-difluoro-cis-13-;
cis-4,5-didehydro-15-methyl-16,16-difluoro-cis-13-;
cis-4,5-didehydro-17-phenyl-18,19,20-trinor-cis-13-;
cis-4,5-didehydro-17-(m-trifluoromethylphenyl)-18,19,20-trinor-cis-13-;
cis-4,5-didehydro-17-(m-chlorophenyl)-18,19,20-trinor-cis-13-;
cis-4,5-didehydro-17-(p-fluorophenyl)-18,19,20-trinor-cis-13-;
cis-4,5-didehydro-15-methyl-17-phenyl-18,19,20-trinor-cis-13-;
cis-4,5-didehydro-16-methyl-17-phenyl-18,19,20-trinor-cis-13-;
cis-4,5-didehydro-16,16-dimethyl-17-phenyl-18,19,20-trinor-cis-13-;
cis-4,5-didehydro-16-fluoro-17-phenyl-18,19,20-trinor-cis-13-;
cis-4,5-didehydro-16,16-difluoro-17-phenyl-18,19,20-trinor-cis-13-;
cis-4,5-didehydro-15-methyl-16,16-difluoro-17-phenyl-18,19,20-trinor-cis-13-;
cis-4,5-didehydro-16-phenoxy-17,18,19,20-tetranor-cis-13-;
cis-4,5-didehydro-15-methyl-16-phenoxy-17,18,19,20-tetranor-cis-13-;
cis-4,5-didehydro-16-(m-trifluoromethylphenoxy)-17,18,19,20-tetranor-cis-13-;
cis-4,5-didehydro-16-(m-chlorophenoxy)-17,18,19,20-tetranor-cis-13-;
cis-4,5-didehydro-16-(p-fluorophenoxy)-17,18,19,20-tetranor-cis-13-;
cis-4,5-didehydro-16-phenoxy-18,19,20-trinor-cis-13-;
cis-4,5-didehydro-15-methyl-16-phenoxy-18,19,20-trinor-cis-13-;
cis-4,5-didehydro-16-methyl-16-phenoxy-18,19,20-trinor-cis-13-;
5-oxa-;
5-oxa-15-methyl-;
5-oxa-16-methyl-;
5-oxa-16,16-dimethyl-;
5-oxa-16-fluoro-;
5-oxa-16,16-difluoro-;
5-oxa-15-methyl-16,16-difluoro-;
5-oxa-17-phenyl-18,19,20-trinor-;
5-oxa-17-(m-trifluoromethylphenyl)-18,19,20-trinor-;
5-oxa-17-(m-chlorophenyl)-18,19,20-trinor-;
5-oxa-17-(p-fluorophenyl)-18,19,20-trinor-;
5-oxa-15-methyl-17-phenyl-18,19,20-trinor-;
5-oxa-16-methyl-17-phenyl-18,19,20-trinor-;
5-oxa-16,16-dimethyl-17-phenyl-18,19,20-trinor-;
5-oxa-16-fluoro-17-phenyl-18,19,20-trinor-;

5-oxa-16,16-difluoro-17-phenyl-18,19,20-trinor-;
5-oxa-15-methyl-16,16-difluoro-17-phenyl-18,19,20-trinor-;
5-oxa-16-phenoxy-17,18,19,20-tetranor-;
5-oxa-16-(m-trifluoromethylphenoxy)-17,18,19,20-tetranor-;
5-oxa-16-(m-chlorophenoxy)-17,18,19,20-tetranor-;
5-oxa-16-(p-fluorophenoxy)-17,18,19,20-tetranor-;
5-oxa-15-methyl-16-phenoxy-17,18,19,20-tetranor-;
5-oxa-16-phenoxy-18,19,20-trinor-;
5-oxa-15-methyl-16-phenoxy-18,19,20-trinor-;
5-oxa-16-methyl-16-phenoxy-18,19,20-trinor-;
5-oxa-13,14-didehydro;
5-oxa-15-methyl-13,14-didehydro-;
5-oxa-16-methyl-13,14-didehydro-;
5-oxa-16,16-dimethyl-13,14-didehydro-;
5-oxa-16-fluoro-13,14-didehydro-;
5-oxa-16,16-difluoro-13,14-didehydro-;
5-oxa-15-methyl-16,16-difluoro-13,14-didehydro-;
5-oxa-17-phenyl-18,19,20-trinor-13,14-didehydro-;
5-oxa-17-(m-trifluoromethylphenyl)-18,19,20-trinor-13,14-didehydro-;
5-oxa-17-(m-chlorophenyl)-18,19,20-trinor-13,14-didehydro-;
5-oxa-17-(p-fluorophenyl)-18,19,20-trinor-13,14-didehydro-;
5-oxa-15-methyl-17-phenyl-18,19,20-trinor-13,14-didehydro-;
5-oxa-16-methyl-17-phenyl-18,19,20-trinor-13,14-didehydro-;
5-oxa-16,16-dimethyl-17-phenyl-18,19,20-trinor-13,14-didehydro-;
5-oxa-16-fluoro-17-phenyl-18,19,20-trinor-13,14-didehydro-;
5-oxa-16,16-difluoro-17-phenyl-18,19,20-trinor-13,14-dihydro-;
5-oxa-16-phenoxy-17,18,19,20-tetranor-13,14-didehydro-;
5-oxa-16-(m-trifluoromethylphenoxy)-17,18,19,20-tetranor-13,14-didehydro-;
5-oxa-16-(m-chlorophenoxy)-17,18,19,20-tetranor-13,14-didehydro-;
5-oxa-15-methyl-16-phenoxy-17,18,19,20-tetranor-13,14-didehydro-;
5-oxa-16-phenoxy-18,19,20-trinor-13,14-didehydro-;
5-oxa-16-methyl-16-phenoxy-18,19,20-trinor-13,14-didehydro-;
5-oxa-13,14-dihydro-;
5-oxa-15-methyl-13,14-dihydro-;
5-oxa-16-methyl-13,14-dihydro-;
5-oxa-16,16-dimethyl-13,14-dihydro-;
5-oxa-16-fluoro-13,14-dihydro-;
5-oxa-16,16-difluoro-13,14-dihydro-;
5-oxa-15-methyl-16,16-tetrafluoro-13,14-dihydro-;
5-oxa-17-phenyl-18,19,20-trinor-13,14-dihydro-;
5-oxa-17-(m-trifluoromethylphenyl)-18,19,20-trinor-13,14-dihydro-;
5-oxa-17-(m-chlorophenyl)-18,19,20-trinor-13,14-dihydro-;
5-oxa-17-(p-fluorophenyl)-18,19,20-trinor-13,14-dihydro-;
5-oxa-15-methyl-17-(p-fluorophenyl)-18,19,20-trinor-13,14-dihydro-;
5-oxa-15-methyl-17-phenyl-18,19,20-trinor-13,14-dihydro-;
5-oxa-16-methyl-17-phenyl-18,19,20-trinor-13,14-dihydro-;
5-oxa-16,16-dimethyl-17-phenyl-18,19,20-trinor-13,14-dihydro-;
5-oxa-16-fluoro-17-phenyl-18,19,20-dihydro-;
5-oxa-16,16-difluoro-17-phenyl-18,19,20-dihydro-;
5-oxa-16-phenoxy-17,18,19,20-tetranor-13,14-dihydro-;
5-oxa-16-(m-trifluoromethylphenoxy)-17,18,19,20-tetranor-13,14-dihydro-;
5-oxa-16-(m-chlorophenoxy)-17,18,19,20-tetranor-13,14-dihydro-;
5-oxa-16-(p-fluorophenoxy)-17,18,19,20-tetranor-13,14-dihydro-;
5-oxa-15-methyl-16-phenoxy-17,18,19,20-tetranor-13,14-dihydro-;
5-oxa-16-phenoxy-18,19,20-trinor-13,14-dihydro-;
5-oxa-15-methyl-16-phenoxy-18,19,20-trinor-13,14-dihydro-;
5-oxa-16-methyl-16-phenoxy-18,19,20-trinor-13,14-dihydro-;
5-oxa-cis-13-;
5-oxa-15-methyl-cis-13-;
5-oxa-16-methyl-cis-13-;
5-oxa-16,16-dimethyl-cis-13-;
5-oxa-16-fluoro-cis-13-;
5-oxa-16,16-difluoro-cis-13-;
5-oxa-15-methyl-16,16-difluoro-cis-13-;
5-oxa-17-phenyl-18,19,20-trinor-cis-13-;
5-oxa-17-(m-trifluoromethylphenyl)-18,19,20-trinor-cis-13-;
5-oxa-17-(m-chlorophenyl)-18,19,20-trinor-cis-13-;
5-oxa-17-(p-fluorophenyl)-18,19,20-trinor-cis-13-,
5-oxa-15-methyl-17-phenyl-18,19,20-trinor-cis-13-;
5-oxa-16-methyl-17-phenyl-18,19,20-trinor-cis-13-;
5-oxa-16,16-dimethyl-17-phenyl-18,19,20-trinor-cis-13-;
5-oxa-16-fluoro-17-phenyl-18,19,20-trinor-cis-13-;
5-oxa-16,16-difluoro-17-phenyl-18,19,20-trinor-cis-13-;
5-oxa-15-methyl-16,16-difluoro-17-phenyl-18,19,20-trinor-cis-13-;
5-oxa-16-phenoxy-17,18,19,20-tetranor-cis-13-;
5-oxa-15-methyl-16-phenoxy-17,18,19,20-tetranor-cis-13-;
5-oxa-16-(m-trifluoromethylphenoxy)-17,18,19,20-tetranor-cis-13-;
5-oxa-16-(m-chlorophenoxy)-17,18,19,20-tetranor-cis-13-;
5-oxa-16-(p-fluorophenoxy)-17,18,19,20-tetranor-cis-13-;
5-oxa-16-phenoxy-18,19,20-trinor-cis-13-;
5-oxa-15-methyl-16-phenoxy-18,19,20-trinor-cis-13-;
5-oxa-16-methyl-16-phenoxy-18,19,20-trinor-cis-13-;
4-oxa-;
4-oxa-15-methyl-;
4-oxa-16-methyl-;
4-oxa-16,16-dimethyl-;
4-oxa-16-fluoro-;
4-oxa-16,16-difluoro-;
4-oxa-15-methyl-16,16-difluoro-;
4-oxa-17-phenyl-18,19,20-trinor-;
4-oxa-17-(m-trifluoromethylphenyl)-18,19,20-trinor-;
4-oxa-17-(m-chlorophenyl)-18,19,20-trinor-;
4-oxa-17-(p-fluorophenyl)-18,19,20-trinor-;
4-oxa-15-methyl-17-phenyl-18,19,20-trinor-;
4-oxa-16-methyl-17-phenyl-18,19,20-trinor-;
4-oxa-16,16-dimethyl-17-phenyl-18,19,20-trinor-;
4-oxa-16-fluoro-17-phenyl-18,19,20-trinor-;
4-oxa-16,16-difluoro-17-phenyl-18,19,20-trinor-;
4-oxa-15-methyl-16,16-difluoro-17-phenyl-18,19,20-trinor-;
4-oxa-16-phenoxy-17,18,19,20-tetranor-;

4-oxa-16-(m-trifluoromethylphenoxy)-17,18,19,20-tetranor-;
4-oxa-16-(m-chlorophenoxy)-17,18,19,20-tetranor-;
4-oxa-16-(p-fluorophenoxy)-17,18,19,20-tetranor-;
4-oxa-15-methyl-16-phenoxy-17,18,19,20-tetranor-;
4-oxa-16-phenoxy-18,19,20-trinor-;
4-oxa-15-methyl-16-phenoxy-18,19,20-trinor-;
4-oxa-16-methyl-16-phenoxy-18,19,20-trinor-;
4-oxa-16-methyl-13,14-didehydro-;
4-oxa-16,16-dimethyl-13,14-didehydro-;
4-oxa-16-fluoro-13,14-didehydro-;
4-oxa-16,16-difluoro-13,14-didehydro-;
4-oxa-15-methyl-16,16-difluoro-13,14-didehydro-;
4-oxa-17-phenyl-18,19,20-trinor-13,14-didehydro-;
4-oxa-15-methyl-17-phenyl-18,19,20-trinor-13,14-didehydro-;
4-oxa-17-(m-trifluoromethylphenyl)-18,19,20-trinor-13,14-didehydro-;
4-oxa-17-(m-chlorophenyl)-18,19,20-trinor-13,14-didehydro-;
4-oxa-17-(p-fluorophenyl)-18,19,20-trinor-13,14-didehydro-;
4-oxa-16-methyl-17-phenyl-18,19,20-trinor-13,14-didehydro-;
4-oxa-16,16-dimethyl-17-phenyl-18,19,20-trinor-13,14-didehydro-;
4-oxa-16-fluoro-17-phenyl-18,19,20-trinor-13,14-didehydro-;
4-oxa-16,16-difluoro-17-phenyl-18,19,20-trinor-13,14-dihydro-;
4-oxa-16-phenoxy-17,18,19,20-tetranor-13,14-didehydro-;
4-oxa-16-(m-trifluoromethylphenoxy)-17,18,19,20-tetranor-13,14-didehydro-;
4-oxa-16-(m-chlorophenoxy)-17,18,19,20-tetranor-13,14-didehydro-;
4-oxa-15-methyl-16-phenoxy-17,18,19,20-tetranor-;13,14-didehydro-;
4-oxa-15-methyl-17-phenyl-18,19,20-trinor-13,14-dihydro-;
4-oxa-17-(m-trifluoromethylphenyl)-18,19,20-trinor-13,14-dihydro-;
4-oxa-17-(m-chlorophenyl)-18,19,20-trinor-13,14-dihydro-;
4-oxa-17-(p-fluorophenyl)-18,19,20-trinor-13,14-dihydro-;
4-oxa-15-methyl-17-(p-fluorophenyl)-18,19,20-trinor-13,14-dihydro-;
4-oxa-16-methyl-17-phenyl-18,19,20-trinor-13,14-dihydro-;
4-oxa-16,16-dimethyl-17-phenyl-18,19,20-trinor-13,14-dihydro-;
4-oxa-16-fluoro-17-phenyl-18,19,20-dihydro-;
4-oxa-16,16-difluoro-17-phenyl-18,19,20-dihydro-;
4-oxa-16-phenoxy-17,18,19,20-tetranor-13,14-dihydro-;
4-oxa-16-(m-trifluoromethylphenoxy)-17,18,19,20-tetranor-13,14-dihydro-;
4-oxa-16-(m-chlorophenoxy)-17,18,19,20-tetranor-13,14-dihydro-;
4-oxa-16-(p-fluorophenoxy)-17,18,19,20-tetranor-13,14-dihydro-;
4-oxa-15-methyl-16-phenoxy-17,18,19,20-tetranor-13,14-dihydro-;
4-oxa-16-phenoxy-18,19,20-trinor-13,14-dihydro-;
4-oxa-15-methyl-16-phenoxy-18,19,20-trinor-13,14-dihydro-;
4-oxa-16-methyl-16-phenoxy-18,19,20-trinor-13,14-dihydro-;

4-oxa-cis-13-;
4-oxa-15-methyl-cis-13-;
4-oxa-16-methyl-cis-13-;
4-oxa-16,16-dimethyl-cis-13-;
4-oxa-16-fluoro-cis-13-;
4-oxa-16,16-difluoro-cis-13-;
4-oxa-15-methyl-16,16-difluoro-cis-13-;
4-oxa-17-phenyl-18,19,20-trinor-cis-13-;
4-oxa-17-(m-trifluoromethylphenyl)-18,19,20-trinor-cis-13-;
4-oxa-17-(m-chlorophenyl)-18,19,20-trinor-cis-13-;
4-oxa-17-(p-fluorophenyl)-18,19,20-trinor-cis-13-;
4-oxa-15-methyl-17-phenyl-18,19,20-trinor-cis-13-;
4-oxa-16-methyl-17-phenyl-18,19,20-trinor-cis-13-;
4-oxa-16,16-dimethyl-17-phenyl-18,19,20-trinor-cis-13-;
4-oxa-16-fluoro-17-phenyl-18,19,20-trinor-cis-13-;
4-oxa-16,16-difluoro-17-phenyl-18,19,20-trinor-cis-13-;
4-oxa-15-methyl-16,16-difluoro-17-phenyl-18,19,20-trinor-cis-13-;
4-oxa-16-phenoxy-17,18,19,20-tetranor-cis-13-;
4-oxa-16-(m-trifluoromethylphenoxy)-17,18,19,20-tetranor-cis-13-;
4-oxa-16-(m-chlorophenoxy)-17,18,19,20-tetranor-cis-13-;
4-oxa-16-(p-fluorophenoxy)-17,18,19,20-tetranor-cis-13-;
4-oxa-15-methyl-16-phenoxy-17,18,19,20-tetranor-cis-13-;
4-oxa-16-phenoxy-18,19,20-trinor-cis-13-;
4-oxa-15-methyl-16-phenoxy-18,19,20-trinor-cis-13-;
4-oxa-16-methyl-16-phenoxy-18,19,20-trinor-cis-13-;
trans-2,3-didehydro-;
trans-2,3-didehydro-15-methyl-;
trans-2,3-didehydro-16-methyl-;
trans-2,3-didehydro-16,16-dimethyl-;
trans-2,3-didehydro-16-fluoro-;
trand-2,3-didehydro-16,16-difluoro-;
trans-2,3-didehydro-15-methyl-16,16-difluoro-;
trans-2,3-didehydro-17-phenyl-18,19,20-trinor-;
trans-2,3-didehydro-17-(m-trifluoromethylphenyl)-18,19,20-trinor-;
trans-2,3-didehydro-17-(m-chlorophenyl)-18,19,20-trinor-;
trans-2,3-didehydro-17-(p-fluorophenyl)-18,19,20-trinor-;
trans-2,3-didehydro-15-methyl-17-phenyl-18,19,20-trinor-;
trans-2,3-didehydro-16-methyl-17-phenyl-18,19,20-trinor-;
trans-2,3-didehydro-16,16-dimethyl-17-phenyl-18,19,20-trinor-;
trans-2,3-didehydro-16-fluoro-17-phenyl-18,19,20-trinor-;
trans-2,3-didehydro-16,16-difluoro-17-phenyl-18,19,20-trinor-;
trans-2,3-didehydro-15-methyl-16,16-difluoro-17-phenyl-18,19,20-trinor-;
trans-2,3-didehydro-16-phenoxy-17,18,19,20-tetranor-;
trans-2,3-didehydro-15-methyl-16-phenoxy-17,18,19,20-tetranor-;
trans-2,3-didehydro-16-(m-trifluoromethylphenoxy)-17,18,19,20-tetranor-;
trans-2,3-didehydro-16-(m-chlorophenoxy)-17,18,19,20-tetranor-;
trans-2,3-didehydro-16-(p-fluorophenoxy)-17,18,19,20-tetranor-;
trans-2,3-didehydro-16-phenoxy-18,19,20-trinor-;

trans-2,3-didehydro-15-methyl-16-phenoxy-18,19,20-trinor-;
trans-2,3-didehydro-15-methyl-16-phenoxy-18,19,20-trinor-;
trans-2,3-didehydro-16-methyl-13,14-didehydro-;
trans-2,3-didehydro-16,16-dimethyl-13,14-didehydro-;
trans-2,3-didehydro-16-fluoro-13,14-didehydro-;
trans-2,3-didehydro-16,16-difluoro-13,14-didehydro-;
trans-2,3-didehydro-15-methyl-16,16-difluoro-13,14-didehydro-;
trans-2,3-didehydro-17-phenyl-18,19,20-trinor-13,14-didehydro-;
trans-2,3-didehydro-17-(m-trifluoromethylphenyl)-18,19,20-trinor-13,14-didehydro-;
trans-2,3-didehydro-17-(m-chlorophenyl)-18,19,20-trinor-13,14-didehydro-;
trans-2,3-didehydro-17-(p-fluorophenyl)-18,19,20-trinor-13,14-didehydro-;
trans-2,3-didehydro-15-methyl-17-phenyl-18,19,20-trinor-13,14-didehydro-;
trans-2,3-didehydro-16-methyl-17-phenyl-18,19,20-trinor-13,14-didehydro-;
trans-2,3-didehydro-16,16-dimethyl-17-phenyl-18,19,20-trinor-13,14-didehydro-;
trans-2,3-didehydro-16-fluoro-17-phenyl-18,19,20-trinor-13,14-didehydro-;
trans-2,3-didehydro-16,16-difluoro-17-phenyl-18,19,20-trinor-13,14-didehydro-;
trans-2,3-didehydro-16-phenoxy-17,18,19,20-tetranor-13,14-didehydro-;
trans-2,3-didehydro-15-methyl-16-phenoxy-17,18,19,20-tetranor-13,14-didehydro-;
trans-2,3-didehydro-16-(m-trifluoromethylphenoxy)-17,18,19,20-tetranor-13,14-didehydro-;
trans-2,3-didehydro-16-(m-chlorophenoxy)-17,18,19,20-tetranor-13,14-didehydro-;
trans-2,3-didehydro-16-phenoxy-18,19,20-trinor-13,14-didehydro-;
trans-2,3-didehydro-16-methyl-16-phenoxy-18,19,20-trinor-13,14-didehydro-;
trans-2,3-didehydro-13,14-dihydro-;
trans-2,3-didehydro-15-methyl-13,14-dihydro-;
trans-2,3-didehydro-16-methyl-13,14-dihydro-;
trans-2,3-didehydro-16,16-dimethyl-13,14-dihydro-;
trans-2,3-didehydro-16-fluoro-13,14-dihydro-;
trans-2,3-didehydro-16,16-difluoro-13,14-dihydro-;
trans-2,3-didehydro-17-phenyl-18,19,20-trinor-13,14-dihydro-;
trans-2,3-didehydro-15-methyl-17-phenyl-18,19,20-trinor-13,14-dihydro-;
trans-2,3-didehydro-17-(m-trifluoromethylphenyl)-18,19,20-trinor-13,14-dihydro-;
trans-2,3-didehydro-17-(m-chlorophenyl)-18,19,20-trinor-13,14-dihydro-;
trans-2,3-didehydro-17-(p-fluorophenyl)-18,19,20-trinor-13,14-dihydro-;
trans-1,3-didehydro-15-methyl-16,16-tetrafluoro-13,14-dihydro-;
trans-2,3-didehydro-15-methyl-17-(p-fluorophenyl)-18,19,20-trinor-13,14-dihydro-;
trans-2,3-didehydro-16-methyl-17-phenyl-18,19,20-trinor-13,14-dihydro-;
trans-2,3-didehydro-16,16-dimethyl-17-phenyl-18,19,20-trinor-13,14-dihydro-;
trans-2,3-didehydro-16-fluoro-17-phenyl-18,19,20-dihydro-;
trans-2,3-didehydro-16,16-difluoro-17-phenyl-18,19,20-trinor-dihydro-;
trans-2,3-didehydro-16-phenoxy-17,18,19,20-tetranor-13,14-dihydro-;
trans-2,3-didehydro-15-methyl-16-phenoxy-17,18,19,20-tetranor-13,14-dihydro-;
trans-2,3-didehydro-16-(m-trifluoromethylphenoxy)-17,18,19,20-tetranor-13,14-dihydro-;
trans-2,3-didehydro-16-(m-chlorophenoxy)-17,18,19,20-tetranor-13,14-dihydro-;
trans-2,3-didehydro-16-(p-fluorophenoxy)-17,18,19,20-tetranor-13,14-dihydro-;
trans-2,3-didehydro-16-phenoxy-18,19,20-trinor-13,14-dihydro-;
trans-1,3-didehydro-15-methyl-16-phenoxy-18,19,20-trinor-13,14-dihydro-;
trans-2,3-didehydro-16-methyl-16-phenoxy-18,19,20-trinor-13,14-dihydro-;
trans-2,3-didehydro-cis-13-;
trans-2,3-didehydro-15-methyl-cis-13-;
trans-2,3-didehydro-16-methyl-cis-13-;
trans-2,3-didehydro-16,16-dimethyl-cis-13-;
trans-2,3-didehydro-16-fluoro-cis-13-;
trans-2,3-didehydro-16,16-difluoro-cis-13-;
trans-2,3-didehydro-15-methyl-16,16-difluoro-cis-13-;
trans-2,3-didehydro-17-phenyl-18,19,20-trinor-cis-13-;
trans-2,3-didehydro-17-(m-trifluoromethylphenyl)-18,19,20-trinor-cis-13-;
trans-2,3-didehydro-17-(m-chlorophenyl)-18,19,20-trinor-cis-13-;
trans-2,3-didehydro-17-(p-fluorophenyl)-18,19,20-trinor-cis-13-;
trans-2,3-didehydro-15-methyl-17-phenyl-18,19,20-trinor-cis-13-;
trans-2,3-didehydro-16-methyl-17-phenyl-18,19,20-trinor-cis-13-;
trans-2,3-didehydro-16,16-dimethyl-17-phenyl-18,19,20-trinor-cis-13-;
trans-2,3-didehydro-16-fluoro-17-phenyl-18,19,20-trinor-cis-13-;
trans-2,3-didehydro-16,16-difluoro-17-phenyl-18,19,20-trinor-cis-13-;
trans-2,3-didehydro-15-methyl-16,16-difluoro-17-phenyl-18,19,20-trinor-cis-13-;
trans-2,3-didehydro-16-phenoxy-17,18,19,20-tetranor-cis-13-;
trans-2,3-didehydro-16-(m-trifluoromethylphenoxy)-17,18,19,20-tetranor-cis-13-;
trans-2,3-didehydro-16-(m-chlorophenoxy)-17,18,19,20-tetranor-cis-13-;
trans-2,3-didehydro-16-(p-fluorophenoxy)-17,18,19,20-tetranor-cis-13-;
trans-2,3-didehydro-15-methyl-16-phenoxy-17,18,19,20-tetranor-cis-13-;
trans-2,3-didehydro-16-phenoxy-18,19,20-trinor-cis-13-;
trans-2,3-didehydro-15-methyl-16-phenoxy-18,19,20-trinor-cis-13-; and
trans-2,3-didehydro-16-methyl-16-phenoxy-18,19,20-trinor-cis-13-.

FORMULAS

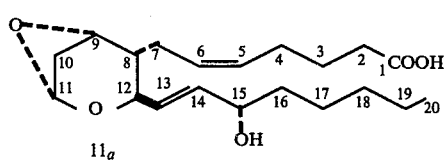

I

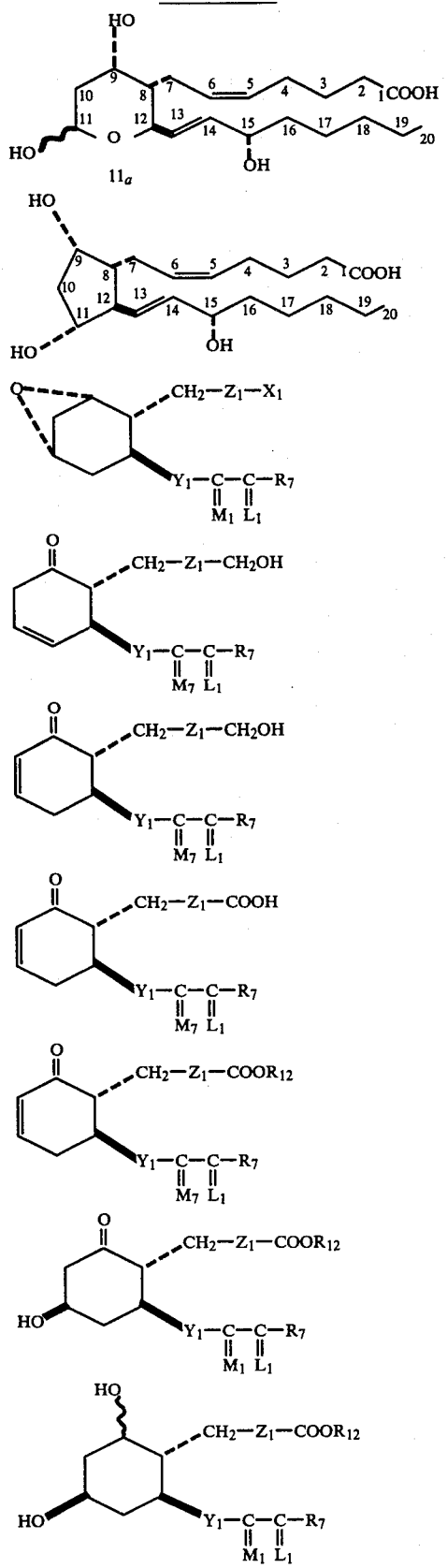
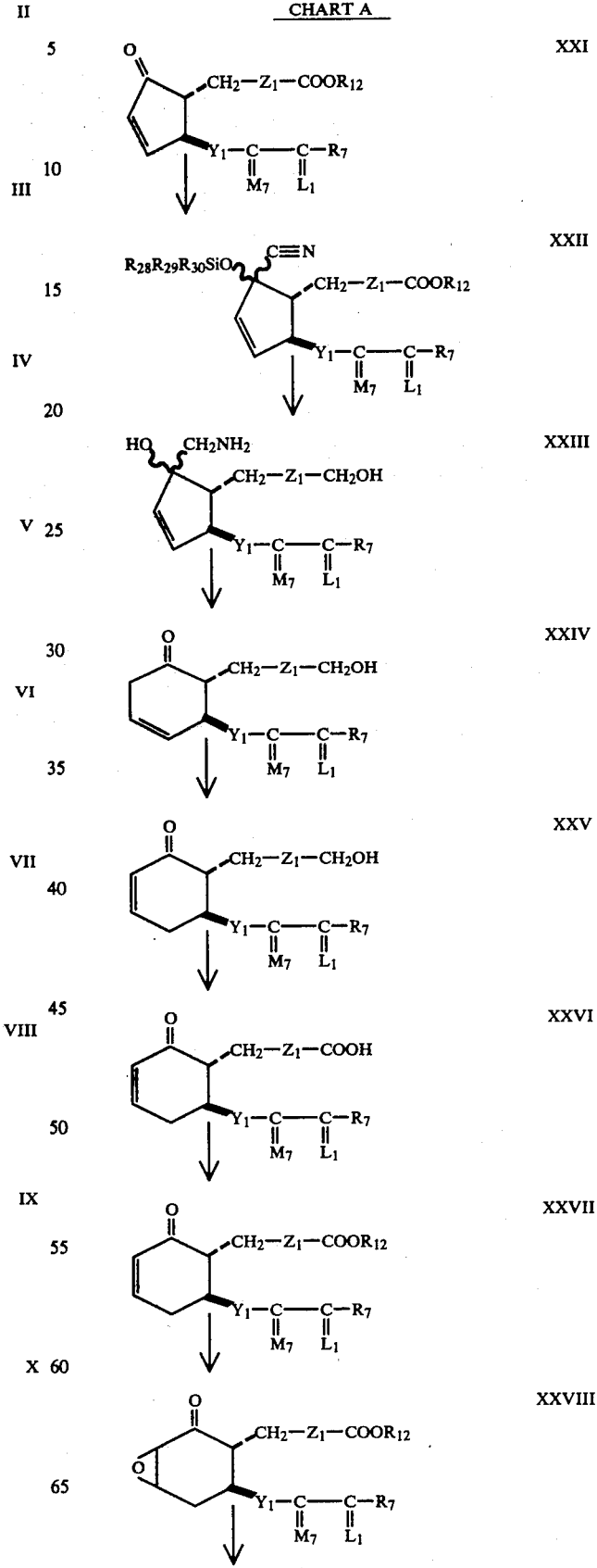

CHART A
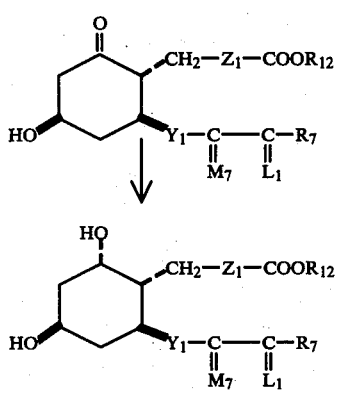
XXIX
XXX
CHART B
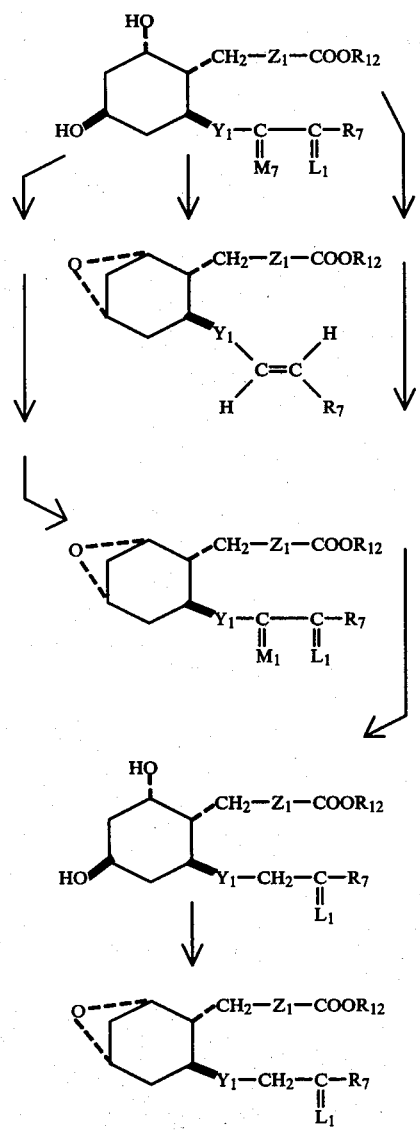
XXXI
XXXII
XXXIII
XXXIV
XXXV
CHART C
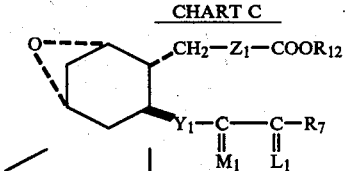   XLI
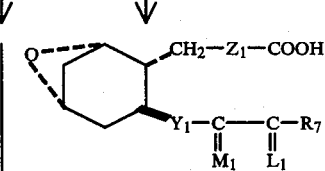   XLII
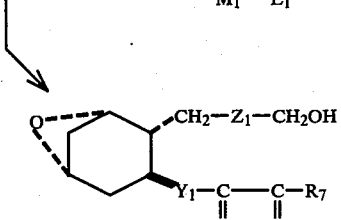   XLIII
   XLIV
   XLV
   XLVI
I claim:
1. A thromboxane analog of formula
wherein $Y_1$ is
 (1) trans—CH=CH—,
 (2) cis—CH=CH—,
 (3) —CH$_2$CH$_2$—, or
 (4) —C≡C—,
wherein $M_1$ is $\alpha R_5$:$\beta$-OH, $\alpha$OH:$\beta$-$R_5$, or $\alpha$-H:$\beta$H, wherein $R_5$ is hydrogen or methyl, and wherein $L_1$ is α-$R_3$:β-$R_4$, α-$R_4$:β-$R_3$, or a mixture of α-$R_3$:β-$R_4$ and β-$R_3$:α-$R_4$, wherein $R_3$ and $R_4$ are hydrogen, methyl, or fluoro, being the same or different, with the proviso that one of $R_3$ and $R_4$ is fluoro only when the other is hydrogen or fluoro, or wherein —C($M_1$)—C($L_1$)— is trans—CH=CH—; wherein $Z_1$ is
- (1) cis—CH=CH—$CH_2$—$(CH_2)_g$—$CH_2$—,
- (2) cis—CH=CH—$CH_2$—$(CH_2)_g$—$CF_2$—,
- (3) cis—$CH_2$—CH=CH—$(CH_2)_g$—$CH_2$—,
- (4) —$(CH_2)_3$—$(CH_2)_g$—$CH_2$—,
- (5) —$(CH_2)_3$—$(CH_2)_g$—$CF_2$—,
- (6) —$CH_2$—O—$CH_2$—$(CH_2)_g$$CH_2$—,
- (7) —$(CH_2)_2$—O—$(CH_2)_g$—$CH_2$—, or
- (8) trans—$CH_2$—$(CH_2)_g$—$CH_2$—CH=CH—;
- (9) —(m—Ph)—O—$(CH_2)_g$—, or
- (10) —(m—Ph)—$CH_2$—$(CH_2)_g$—, wherein g is one, 2, or 3 and —(m—Ph)— is meta-phenylene; wherein $R_7$ is
- (1) —$(CH_2)_m$—$CH_3$, wherein m is an integer from one to 5, inclusive;
- (2) phenoxy;
- (3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
- (4) phenyl;
- (5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
- (6) phenylmethyl, phenylethyl, or phenylpropyl; or
- (7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different; and wherein $X_1$ is —$COOR_1$, wherein $R_1$ is (a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, two, or three chloro or alkyl of one to 3 carbon atoms;
(g) phenyl substituted in the para position by
  (i) —NH—CO—$R_{25}$
  (ii) —CO—$R_{26}$
  (iii) —O—CO—$R_{27}$
  (iv) —CH=N—NH—CO—$NH_2$
  wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is phenyl or acetamidophenyl; inclusive, or a pharmacologically acceptable salt thereof when $R_1$ is hydrogen.

2. A thromboxane analog according to claim 1, wherein $Y_1$ is —C≡C—.

3. 11a-Methano-13,14-didehydro-TXA$_2$, a thromboxane analog according to claim 2.

4. 11a-Methano-13,14-didehydro-15-deoxy-TXA$_2$, a thromboxane analog according to claim 2.

5. 11a-Methano-13,14-didehydro-15-deoxy-15,16-didehydro-TXA$_2$, a thromboxane analog according to claim 2.

6. A thromboxane analog according to claim 1, wherein $Y_1$ is —$CH_2CH_2$—.

7. 11a-Methano-13,14-dihydro-TXA$_2$, a thromboxane analog according to claim 6.

8. 11a-Methano-13,14-dihydro-15-deoxy-TXA$_2$, a thromboxane analog according to claim 6.

9. 11a-Methano-13,14-dihydro-15-deoxy-15,16-didehydro-TXA$_2$, a thromboxane analog according to claim 6.

10. A thromboxane analog according to claim 1, wherein $Y_1$ is cis—CH=CH—.

11. 11a-Methano-cis-13-TXA$_2$, a thromboxane analog according to claim 10.

12. 11a-Methano-cis-13-15-deoxy-TXA$_2$, a thromboxane analog according to claim 10.

13. 11a-Methano-cis-13-15-deoxy-15,16-didehydro-TXA$_2$, a thromboxane analog according to claim 10.

14. A thromboxane analog according to claim 1, wherein $Y_1$ is trans—CH=CH—.

15. A thromboxane analog according to claim 14, wherein $R_7$ is phenoxy or substituted phenoxy.

16. 11a-Methano-16-phenoxy-17,18,19,20-tetranor-TXA$_2$, a thromboxane analog according to claim 15.

17. 11a-Methano-16-phenoxy-15-deoxy-17,18,19,20-tetranor-TXA$_2$, a thromboxane analog according to claim 15.

18. 11a-Methano-16-phenoxy-15-deoxy-15,16-didehydro-17,18,19,20-tetranor-TXA$_2$, a thromboxane analog according to claim 15.

19. A thromboxane analog according to claim 14, wherein $R_7$ is phenyl or substituted phenyl.

20. 11a-Methano-16-phenyl-17,18,19,20-tetranor-TXA$_2$, a thromboxane analog according to claim 19.

21. 11a-Methano-16-phenyl-15-deoxy-17,18,19,20-tetranor-TXA$_2$, a thromboxane analog according to claim 19.

22. 11a-Methano-16-phenyl-15-deoxy-15,16-didehydro-17,18,19,20-tetranor-TXA$_2$, a thromboxane analog according to claim 19.

23. A thromboxane analog according to claim 14, wherein $R_7$ is phenylmethyl or substituted phenylmethyl.

24. 11a-Methano-17-phenyl-18,19,20-trinor-TXA$_2$, a thromboxane analog according to claim 23.

25. 11a-Methano-17-phenyl-15-deoxy-18,19,20-trinor-TXA$_2$, a thromboxane analog according to claim 23.

26. 11a-Methano-17-phenyl-15-deoxy-15,16-didehydro-18,19,20-trinor-TXA$_2$, a thromboxane analog according to claim 23.

27. A thromboxane analog according to claim 14, wherein $R_7$ is —$(CH_2)_m$—$CH_3$.

28. A thromboxane analog according to claim 27, wherein m is 3.

29. A thromboxane analog according to claim 28, wherein $Z_1$ is cis—CH=CH—$CH_2$—$(CH_2)_g$—$CF_2$—.

30. 2,2-Difluoro-11a-methano-TXA$_2$, a thromboxane analog according to claim 29.

31. 2,2-Difluoro-11a-methano-15-deoxy-TXA$_2$, a thromboxane analog according to claim 29.

32. 2,2-Difluoro-11a-methano-15-deoxy-15,16-didehydro-TXA$_2$, a thromboxane analog according to claim 29.

33. A thromboxane analog according to claim 28, wherein $Z_1$ is cis—$CH_2$—CH=CH—$(CH_2)_g$—$CH_2$—.

34. cis-4,5-Didehydro-11a-methano-TXA$_1$, a thromboxane analog according to claim 33.

35. cis-4,5-Didehydro-11a-methano-15-deoxy-TXA$_1$, a thromboxane analog according to claim 33.

36. cis-4,5-Didehydro-11a-methano-15-deoxy-15,16-didehydro-TXA$_1$, a thromboxane analog accoridng to claim 33.

37. A thromboxane analog according to claim 28, wherein Z$_1$ is —(CH$_2$)$_3$—(CH$_2$)$_g$—CH$_2$—.

38. 11a-Methano-TXA$_1$, a thromboxane analog according to claim 37.

39. 11a-Methano-15-deoxy-TXA$_1$, a thromboxane analog according to claim 37.

40. 11a-Methano-15-deoxy-15,16-didehydro-TXA$_1$, a thromboxane analog according to claim 37.

41. A thromboxane analog according to claim 28, wherein Z$_1$ is —(CH$_2$)$_3$—(CH$_2$)$_g$—CF$_2$—.

42. 2,2-Difluoro-11a-methano-TXA$_1$, a thromboxane analog according to claim 41.

43. 2,2-Difluoro-11a-methano-15-deoxy-TXA$_1$, a thromboxane analog according to claim 41.

44. 2,2-Difluoro-11a-methano-15-deoxy-15,16-didehydro-TXA$_1$, a thromboxane analog according to claim 41.

45. A thromboxane analog according to claim 28, wherein Z$_1$ is —CH$_2$—O—CH$_2$—(CH$_2$)$_g$—CH$_2$—.

46. 5-Oxa-11a-methano-TXA$_1$, a thromboxane analog according to claim 45.

47. 5-Oxa-11a-methano-15-deoxy-TXA$_1$, a thromboxane analog according to claim 45.

48. 5-Oxa-11a-methano-15-deoxy-15,16-didehydro-TXA$_1$, a thromboxane analog according to claim 45.

49. A thromboxane analog according to claim 28, wherein Z$_1$ is —(CH$_2$)$_2$—O—(CH$_2$)$_g$—CH$_2$—.

50. 4-Oxa-11a-methano-TXA$_1$, a thromboxane analog according to claim 49.

51. 4-Oxa-11a-methano-15-deoxy-TXA$_1$, a thromboxane analog according to claim 49.

52. 4-Oxa-11a-methano-15-deoxy-15,16-didehydro-TXA$_1$, a thromboxane analog according to claim 49.

53. A thromboxane analog according to claim 28, wherein Z$_1$ is trans—CH$_2$(CH$_2$)$_g$—CH$_2$—CH=CH—.

54. trans-2,3-Didehydro-11a-methano-TXA$_1$, a thromboxane analog according to claim 53.

55. trans-2,3-Didehydro-11a-methano-15-deoxy-TXA$_1$, a thromboxane analog according to claim 53.

56. trans-2,3-Didehydro-11a-methano-15-deoxy-15,16-didehydro-TXA$_1$, a thromboxane analog according to claim 53.

57. A thromboxane analog according to claim 28, wherein Z$_1$ is —(m-Ph)—O—(CH$_2$)$_g$—.

58. 3,7-inter-m-phenylene-4,5,6-trinor-3-oxa-TXA$_1$, 11a-methano a thromboxane analog according to claim 57.

59. 3,7-inter-m-phenylene-4,5,6-trinor-3-oxa-11a-methano-15-deoxy-TXA$_1$, a thromboxane analog according to claim 57.

60. 3,7-inter-m-phenylene-4,5,6-trinor-3-oxa-11a-methano-15-deoxy-15,16-didehydro-TXA$_1$, a thromboxane analog according to claim 57.

61. A thromboxane analog according to claim 28, wherein Z$_1$ is —(m-Ph)—CH$_2$—(CH$_2$)$_g$—.

62. 3,7-inter-m-phenylene-4,5,6-trinor-11a-methano-TXA$_1$, a thromboxane analog according to claim 61.

63. 3,7-inter-m-phenylene-4,5,6-trinor-11a-methano-15-deoxy-TXA$_1$, a thromboxane analog according to claim 61.

64. 3,7-inter-m-phenylene-4,5,6-trinor-11a-methano-15-deoxy-15,16-didehydro-TXA$_1$, a thromboxane analog according to claim 61.

65. A thromboxane analog according to claim 28, wherein Z$_1$ is cis—CH=CH—CH$_2$—(CH$_2$)$_g$—CH$_2$—.

66. A thromboxane analog according to claim 65, wherein g is 3.

67. 2a,2b-dihomo-11a-methano-TXA$_2$, a thromboxane analog according to claim 66.

68. 2a,2b-dihomo-11a-methano-15-deoxy-TXA$_2$, a thromboxane analog according to claim 66.

69. 2a,2b-dihomo-11a-methano-15-deoxy-15,16-didehydro-TXA$_2$, a thromboxane analog according to claim 66.

70. A thromboxane analog according to claim 65, wherein g is one.

71. A thromboxane analog according to claim 70, wherein at least one of R$_3$ and R$_4$ is methyl.

72. A thromboxane analog according to claim 71, wherein R$_3$ and R$_4$ are both methyl.

73. 11a-Methano-16,16-dimethyl-TXA$_2$, a thromboxane analog according to claim 72.

74. 11a-Methano-16,16-dimethyl-15-deoxy-TXA$_2$, a thromboxane analog according to claim 72.

75. A thromboxane analog according to claim 70, wherein at least one of R$_3$ and R$_4$ is fluoro.

76. A thromboxane analog according to claim 75, wherein R$_3$ and R$_4$ are both fluoro.

77. 11a-Methano-16,16-difluoro-TXA$_2$, a thromboxane analog according to claim 76.

78. 11a-Methano-16,16-difluoro-15-deoxy-TXA$_2$, a thromboxane analog accoridng to claim 76.

79. A thromboxane analog according to claim 70, wherein R$_3$ and R$_4$ are both hydrogen.

80. A thromboxane analog according to claim 79, wherein R$_5$ is methyl.

81. 11a-Methano-15-methyl-TXA$_2$, a thromboxane analog according to claim 80.

82. A thromboxane analog according to claim 79, wherein R$_5$ is hydrogen.

83. 11a-Methano-TXA$_2$, a thromboxane analog according to claim 82.

84. 11a-Methano-TXA$_2$, methyl ester, a thromboxane analog according to claim 82.

85. 11a-Methano-15-deoxy-TXA$_2$, a thromboxane analog according to claim 84.

86. 11a-Methano-15-deoxy-TXA$_2$, methyl ester, a thromboxane analog according to claim 84.

87. A thromboxane analog according to claim 70, wherein —C(M$_1$)—C(L$_1$)— is trans-CH=CH—.

88. 11a-Methano-15-deoxy-15,16-didehydro-TXA$_2$, a thromboxane analog according to claim 87.

89. 11a-Methano-15-deoxy-15,16-didehydro-TXA$_2$, methyl ester, a thromboxane analog according to claim 87.

* * * * *

UNITED STATES PATENT OFFICE
CERTIFICATE OF CORRECTION

Patent No. 4,218,378            Dated  19 August 1980

Inventor(s)  Gordon L. Bundy

It is certified that error appears in the above-identified patent and that said Letters Patent are hereby corrected as shown below:

Column 5, lines 25-36, "comounds" should read -- compounds --; line 52, ""20-methyl" or "20-methyl"" should read -- "20-methyl" or 20-ethyl" --;
Column 10, line 19, "2-dluoro-"; should read -- 2-fluro- --;
Column 11, line 57, "tansplant" should read -- transplant --;
Column 15, line 40, "XXXIII and" should read -- XXXII and --;
Column 16, line 39, "Cis-CH=CH-($H_2$)$_3$" should read -- cis-CH=CH-($CH_2$)$_3$ --;
Column 17, line 40, "770 L $cm^{-1}$" should read -- 770 $cm^{-1}$ --;
Column 18, line 33, "20°C" should read -- -20°C --;
Column 19, line 43, "414-4.6" should read -- 4.4-4.6 --;
Column 27, lines 23 and 24, "18,19,20-dihydro-" should read -- 18,19,20-trinor-13,14-dihydro- --;
Column 29, line 54, "15-17-phenyl-" should read -- 15-methyl-17-phenyl- --
Column 50, lines 54-60, should read as follows:

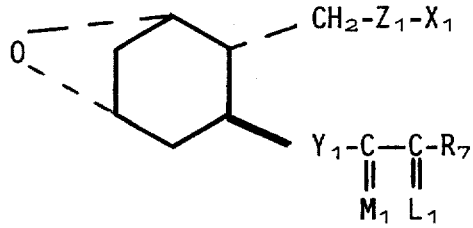

UNITED STATES PATENT OFFICE
CERTIFICATE OF CORRECTION

Patent No. 4,218,378        Dated 19 August 1980

Inventor(s) Gordon L. Bundy

It is certified that error appears in the above-identified patent and that said Letters Patent are hereby corrected as shown below:

Column 50, line 67, "$\alpha R_5:\beta\text{-}OH$, $\alpha OH:\beta\text{-}R_5$, or $\alpha\text{-}H:\beta H$," should read -- $\alpha\text{-}R_5:\beta\text{-}OH$, $\alpha\text{-}OH:\beta\text{-}R_5$, or $\alpha\text{-}H:\beta\text{-}H$, --;

Column 51, line 13, "$-CH_2-O-CH_2-(CH_2)gCH_2-$" should read -- $-CH_2-O-CH_2-(CH_2)g-CH_2-$ --;

Column 53, line 44, "trans-$CH_2(CH_2)g-CH_2-CH=CH-$" should read -- trans-$CH_2-(CH_2)g-CH_2-CH=CH-$ --;

Column 53, line 55-56, "3-oxa-$TXA_1$, 11a-methano" should read -- 3-oxa-11a-methano-$TXA_1$, --;

Signed and Sealed this

*Twenty-first* Day of *September 1982*

[SEAL]

*Attest:*

*Attesting Officer*

GERALD J. MOSSINGHOFF

*Commissioner of Patents and Trademarks*